(12) United States Patent
Wegiel et al.

(10) Patent No.: US 10,512,631 B2
(45) Date of Patent: Dec. 24, 2019

(54) CHALCONE COMPOUNDS

(71) Applicant: Beth Israel Deaconess Medical Center, Inc., Boston, MA (US)

(72) Inventors: Barbara Wegiel, Brighton, MA (US); Lijun Sun, Harvard, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 0 days.

(21) Appl. No.: 15/769,301

(22) PCT Filed: Sep. 23, 2016

(86) PCT No.: PCT/US2016/053369
§ 371 (c)(1),
(2) Date: Apr. 18, 2018

(87) PCT Pub. No.: WO2017/069913
PCT Pub. Date: Apr. 27, 2017

(65) Prior Publication Data
US 2018/0303797 A1    Oct. 25, 2018

Related U.S. Application Data

(60) Provisional application No. 62/245,725, filed on Oct. 23, 2015.

(51) Int. Cl.
*A61K 31/404*    (2006.01)
*A61P 35/02*    (2006.01)
*C07D 209/08*    (2006.01)
*C07D 209/60*    (2006.01)

(52) U.S. Cl.
CPC ........... *A61K 31/404* (2013.01); *A61P 35/02* (2018.01); *C07D 209/60* (2013.01)

(58) Field of Classification Search
CPC ...... A61K 31/404; A61P 35/02; C07D 209/08
USPC .......................................... 514/415; 548/469
See application file for complete search history.

(56) References Cited

U.S. PATENT DOCUMENTS

2004/0229931 A1* 11/2004 Mailliet ............... C07D 209/08
514/414

FOREIGN PATENT DOCUMENTS

| EP | 0125695 | 11/1984 | |
|---|---|---|---|
| WO | WO-0146110 A2 * | 6/2001 | ........... C07C 49/217 |
| WO | WO 01/68564 | 9/2001 | |

OTHER PUBLICATIONS

STN Registry database entry: CAS RN 1322917-12-3 (Entered STN: Aug. 25, 2011). (Year: 2011).*
STN Registry database entry: CAS RN 1322806-47-2 (Entered STN: Aug. 24, 2011). (Year: 2011).*
STN Registry database entry: CAS RN 1071614-16-8 (Entered STN: Nov. 7, 2008) (Year: 2008).*
Bunkoczi et al., "Structural and Functional Characterization of the Human Protein Kinase ASK1," Structure Oct. 16, 2007, 15(10):1215-1226.
Chandran et al., "Gene expression profiles of prostate cancer reveal involvement of multiple molecular pathways in the metastatic process," BMC cancer, Dec. 2007, 7(1):64, 21 pages.
Chin et al., "Hypoxia-inducible factor 1α stabilization by carbon monoxide results in cytoprotective preconditioning," Proc. Natl. Acad. Sci. Mar. 20, 2007, 104(12):5109-5114.
Faidallah et al., "Synthesis of some new 2-oxo-1,4-disubstituted-1,2,5,6-tetrahydro-benzo[h]quinoline-3-carboni triles and their biological evaluation as cytotoxic and antiviral agents", Journal of chemical sciences, May 1, 2012, 124(3):625-631.
International Preliminary Report on Patentability in International Application No. PCT/US2016/053369, dated Apr. 24, 2018, 8 pages.
International Search Report and Written Opinion in International Application No. PCT/US2016/053369, dated Nov. 30, 2016, 14 pages.
Jagtap et al., "Structure-Activity Relationship Study of Tricyclic Necroptosis Inhibitors", Journal of Medicinal Chemistry, Apr. 1, 2007, 50(8):1886-1895.
Li et al., "Elevated STMN1 Expression Correlates with Poor Prognosis in Patients with Pancreatic Ductal Adenocarcinoma," Pathology Oncology Research, Sep. 1, 2015, 21(4):1013-1020.
Morris et al., "AutoDock4 and AutoDockTools4: Automated Docking with Selective Receptor Flexibility," Journal of Computational Chemistry 2009, 30(16):2785-91.
Parveen et al., "Synthesis, biological evaluation and 3D-QSAR studies of new chalcone derivatives as inhibitors of human P-glycoprotein", Bioorganic & Medicinal Chemistry, 2014, 22(7):2311-2319.
Robinson et al., "Synthesis and biological evaluation of aromatic enones related to curcumin", Bioorganic & Medicinal Chemistry, Pergamon, GB, Jun. 2, 2005, 13(12):4007-4013.
Trott et al., "AutoDock Vina: improving the speed and accuracy of docking with a new scoring function, efficient optimization, and multithreading," Journal of Computational Chemistry, Jan. 30, 2010, 31(2):455-461.
Wegiel et al, "Carbon Monoxide Expedites Metabolic Exhaustion to Inhibit Tumor Growth," Cancer research, Dec. 1, 2013, 73(23):7009-7021.
Wegiel et al., "Cell Surface Biliverdin Reductase Mediates Biliverdin-induced Anti-inflammatory Effects via Phosphatidylinositol 3-Kinase and Akt," J Biol. Chem. Aug. 7, 2009, 284(32):21369-78.
Williams et al., "Inhibition of stathmin1 accelerates the metastatic process," Cancer Research Oct. 15, 2012, 72(20):5407-5417.

* cited by examiner

*Primary Examiner* — Matthew P Coughlin
*Assistant Examiner* — Sagar Patel
(74) *Attorney, Agent, or Firm* — Fish & Richardson P.C.

(57) ABSTRACT

This disclosure relates to the compounds of formula (I): [INSERT FORMULA], in which A and R1-R12 are defined in the Specification. The compounds of formula (I) have therapeutic effects, such as treating cancers.

19 Claims, 10 Drawing Sheets

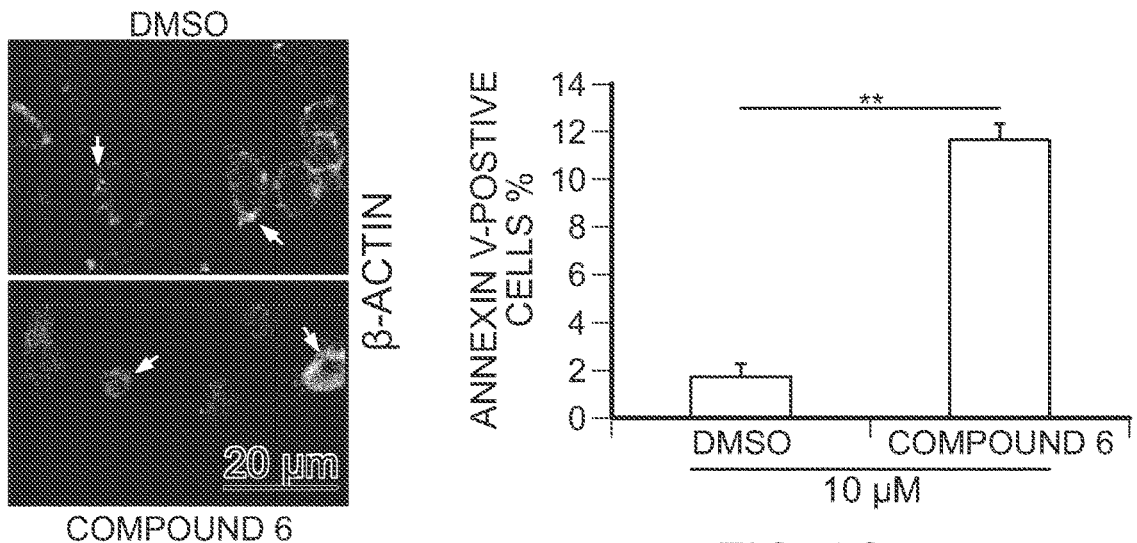
FIG. 1F
FIG. 1G
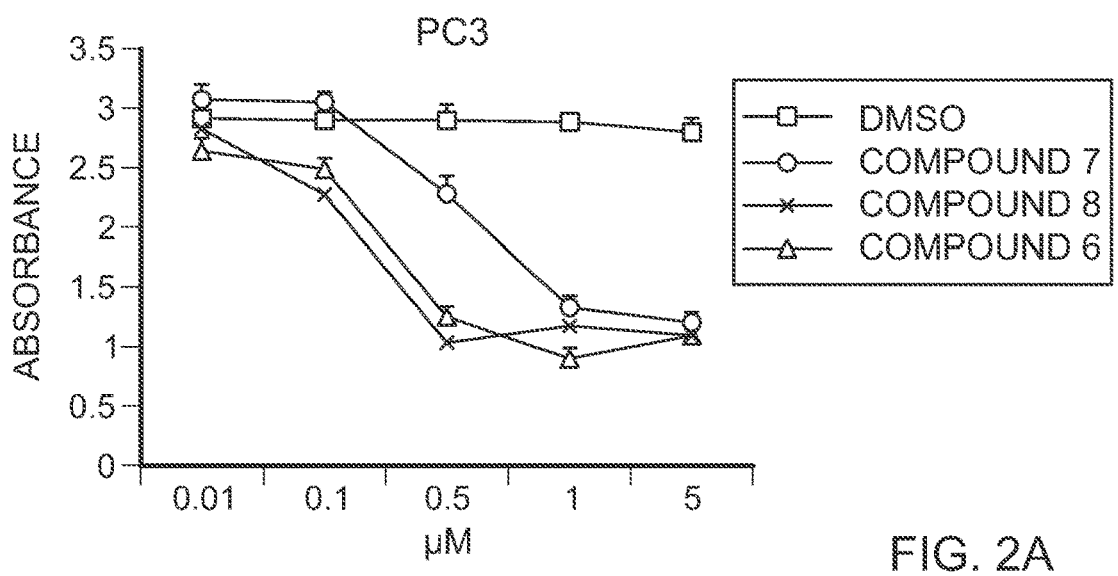
FIG. 2A
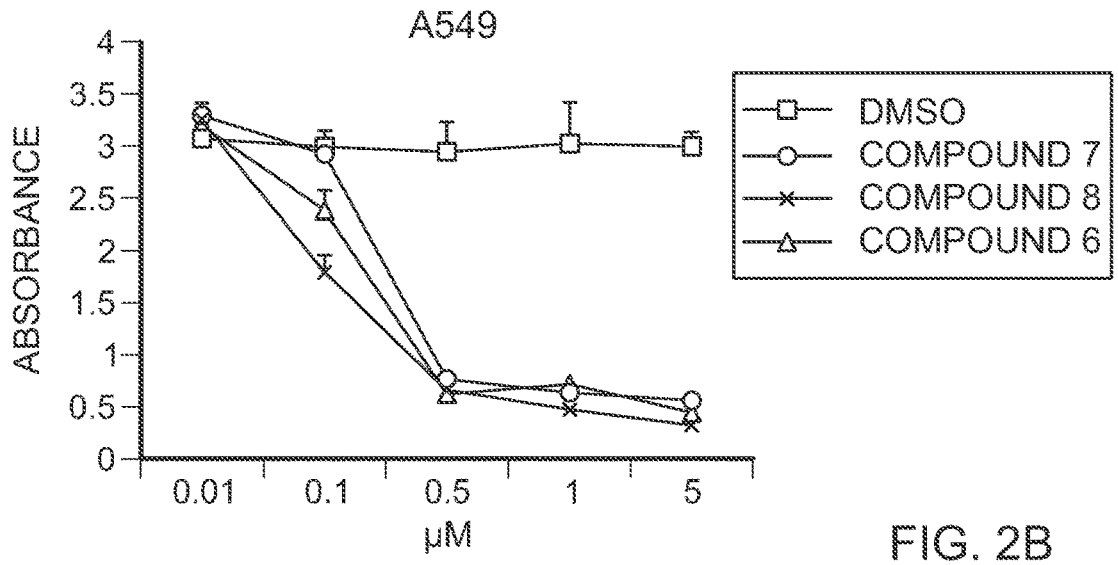
FIG. 2B

CHALCONE COMPOUNDS

CROSS-REFERENCE TO RELATED APPLICATIONS

This application is a U.S. National Phase Application under 35 U.S.C. § 371 of International Patent Application No. PCT/US2016/053369, filed on Sep. 23, 2016, which claims priority under 35 U.S.C § 119(e) to U.S. Provisional Application No. 62/245,725, filed Oct. 23, 2015, the disclosure of which is incorporated herein in its entirety.

TECHNICAL FIELD

This disclosure relates to chalcone compounds, as well as methods of synthesizing and using such compounds.

BACKGROUND

Anti-mitotic agents such as taxanes (e.g., docetaxel) and vinca alkaloids (e.g., vinblastine or vincristine) are among the most effective drugs in treating metastatic diseases, but their benefits are limited by the rapid development of resistance. As such, there is still a need for selective therapeutic agents that not only target cell division and induce early cell death in the primary tumor but also suppress metastatic spread.

Dynamics of microtubules is an important aspect of cell growth. Stathmin (STMN1, OP18, Oncoprotein18) is a microtubule destabilizing protein that plays an important role in the anti-mitotic drug response as it regulates mitotic spindle dynamics involved in cell proliferation and migration/invasion. STMN1 acts directly on α-tubulin polymers in microtubules, promoting their destabilization and depolymerization. Cancer cells utilize STMN1 to accommodate rapid cell division and proliferation. Expression of STMN1 is controlled by common cell cycle regulators such as cyclin-dependent kinase-1 (CDK1), cdc2 kinase, p53 as well as apoptosis signal-regulating kinase 1 (ASK1). Inhibition of STMN1 with small interfering RNA (siRNA) was shown to sensitize cancer cells to 5-FU treatment. Additionally, knockdown of STMN1 blocked tumor growth in vivo in a model of pancreatic cancer. Ribozyme targeting of STMN1 was associated with G2/M arrest and apoptosis of Estrogen Receptor+(ER) and ER− breast cancer cells. However, overexpression of STMN1 blocked metastatic spread in prostate cancer cells and induced growth arrest at the G2/M phase checkpoint in various breast cancer cell lines. STMN1 is also a potential target for modulating tumor angiogenesis as it is a regulator of microtubule dynamics, Rho activity and vascular permeability.

SUMMARY

In one aspect, this disclosure features a compound of formula (I) or a salt thereof:

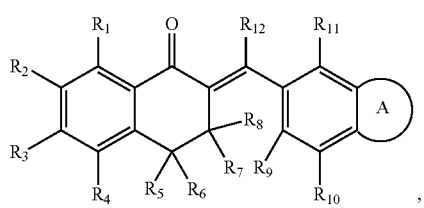

in which A is a five-membered ring or a six-membered ring, each of which optionally contains a heteroatom and is optionally substituted with one or more substituents selected from the group consisting of halo, CN, OR, COOR, C(O)R, $C_1$-$C_{10}$ alkyl, $C_1$-$C_{10}$ arylalkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, and heteroaryl; and each of $R_1$, $R_2$, $R_3$, $R_4$, $R_5$, $R_6$, $R_7$, $R_8$, $R_9$, $R_{10}$, $R_{11}$, and $R_{12}$, independently, is H, halo, CN, OR', COOR', C(O)R', $C_1$-$C_{10}$ alkyl, $C_1$-$C_{10}$ arylalkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl. Each of R and R', independently, is H, $C_1$-$C_{10}$ alkyl, $C_3$-$C_{20}$ cycloalkyl, $C_3$-$C_{20}$ heterocycloalkyl, aryl, or heteroaryl.

In another aspect, this disclosure features a pharmaceutical composition that includes a compound of formula (I) described herein and a pharmaceutically acceptable carrier.

In another aspect, this disclosure features a method of treating cancer in a subject in need thereof. The method includes administering to the subject the pharmaceutical composition described herein in an amount effective to treat the cancer.

In another aspect, this disclosure features a method of destabilizing microtubules in a cell. The method includes contacting the cell with a compound of formula (I) described herein in an amount sufficient to destabilize the microtubules in the cell.

In another aspect, this disclosure features a method of modulating stathmin (STMN1) activity in a cell. The method includes contacting the cell with a compound of formula (I) described herein.

In still another aspect, this disclosure features a method of modulating apoptosis signal-regulating kinase 1 (ASK1) activity in a cell. The method includes contacting the cell with a compound of formula (I) described herein.

Other features, objects, and advantages will be apparent from the description and the claims.

DESCRIPTION OF DRAWINGS

FIGS. 1E and 1F are images showing immunostaining analyses of α-tubulin and β-actin in PC3 cells untreated (control) or treated with DMSO, Compound 6 (1 μM), or docetaxel (20 nM) for 24 hours.

FIG. 1G is a graph showing that treatment of prostate cancer PC3 cells with Compound 6 led to increased number of Annexin V-positive cells.

FIGS. 2A and 2B are graphs showing that apoptosis induction in response to treatment of PC3 cells (2A) and A549 cells (2B) with 0.01-5 μM Compounds 6-8 for 72 hours (n=4, p<0.05 for dose >0.33 μM). Absorbances correspond to the number of alive cells. Average±SD are shown. IC50 PC3: 0.147 μM for Compound 6, 0.449 μM for Compound 7, and 0.106 μM for Compound 8. IC50 A549: 0.208 μM for Compound 6, 0.271 μM for Compound 7, and 0.113 μM for Compound 8.

Like reference symbols in the various drawings indicate like elements.

DETAILED DESCRIPTION

Figure 1A:
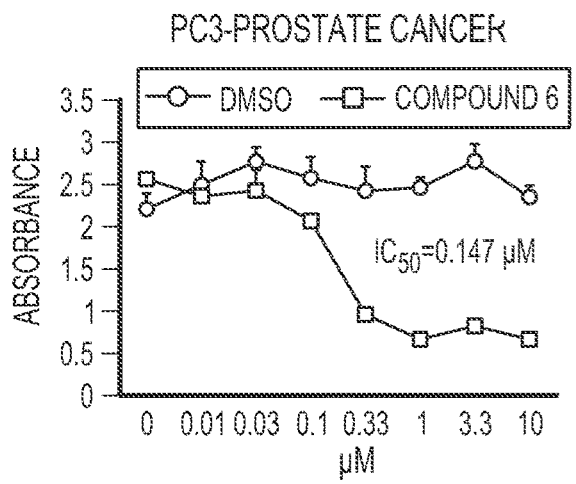
FIGS. 1A-1D are graphs showing the results obtained from crystal violet staining of prostate cancer cells (PC3), lung carcinoma (A549), pancreatic (CLR2119, PAN02) cell lines treated with Compound 6 at various concentrations for 72 hours. Cells were stained with crystal violet and absorbance corresponding to number of alive cells was evaluated at 562 nm. The data are representative for n=6. Averages±SD are shown. P<0.01 for concentrations ≥0.33 μM. IC50 is indicated on the graph for each cell line.
Figure 1B:
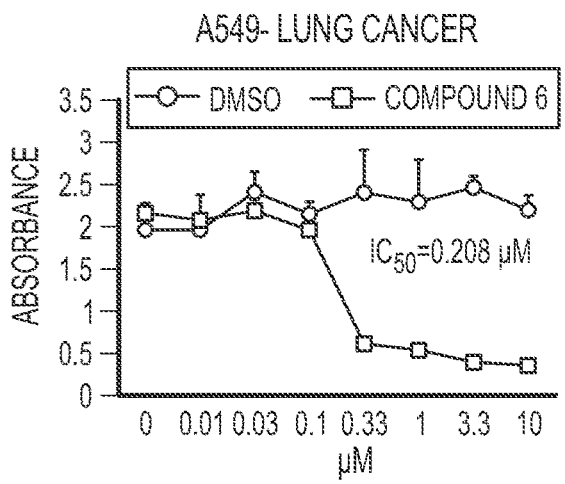
Figure 1C:
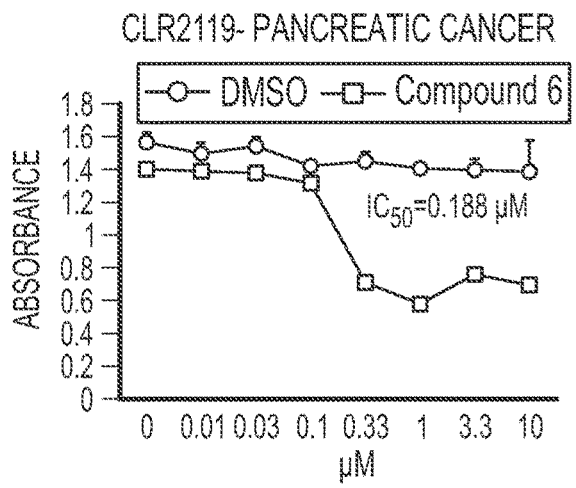
Figure 1D:
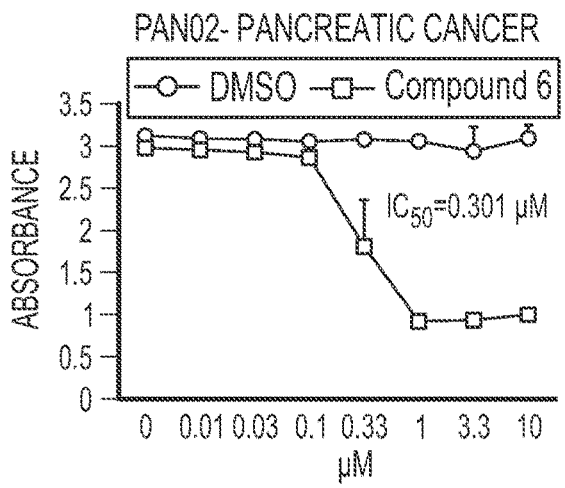

This disclosure generally relates to chalcone compounds, methods of synthesizing these compounds, and their uses (e.g., for treating cancers). In particular, this disclosure is based on the unexpected discovery that certain chalcone compounds (such as those of formula (I) described herein) can destabilize microtubules (e.g., by modulating the activities of ASK1 and/or STMN1) in cancer cells and lead to cancer cell death. It is believed that modulation of the ASK1/STMN1 pathway by the chalcone compounds described herein can allow for broader targeting of cancer cells in different cell cycle phases, while still targeting mitosis and induction of cell death as the end point. It is also believed that targeting ASK1 and its downstream target STMN1 with these chalcone compounds could decrease the levels of α-tubulin monomers available for polymerization and/or promote disassembly of existing microtubules independently of the cell cycle progression.

In some embodiments, the chalcone compounds described herein are those of formula (I) or a salt thereof (e.g., a pharmaceutically acceptable salt thereof):

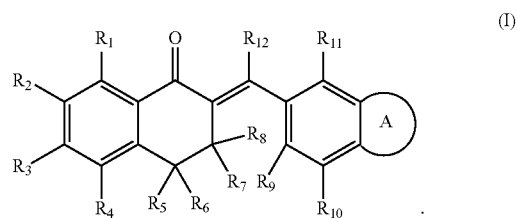

In formula (I), A is a five-membered ring or a six-membered ring, each of which optionally contains a heteroatom and is optionally substituted with one or more substituents selected from the group consisting of halo (e.g., F, Cl, Br, or I), CN, OR, COOR, C(O)R, $C_1$-$C_{10}$ alkyl, $C_1$-$C_{10}$ arylalkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, and heteroaryl; and each of $R_1$, $R_2$, $R_3$, $R_4$, $R_5$, $R_6$, $R_7$, $R_8$, $R_9$, $R_{10}$, $R_{11}$, and $R_{12}$, independently, is H, halo (e.g., F, Cl, Br, or I), CN, OR', COOR', C(O)R', $C_1$-$C_{10}$ alkyl, $C_1$-$C_{10}$ arylalkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl. Each of R and R', independently, is H, $C_1$-$C_{10}$ alkyl, $C_3$-$C_{20}$ cycloalkyl, $C_3$-$C_{20}$ heterocycloalkyl, aryl, or heteroaryl.

The term "alkyl" refers to a saturated, linear or branched hydrocarbon moiety, such as —$CH_3$ or —$CH(CH_3)_2$. The term "alkenyl" refers to a linear or branched hydrocarbon moiety that contains at least one double bond, such as —CH═CH—$CH_3$. The term "alkynyl" refers to a linear or branched hydrocarbon moiety that contains at least one triple bond, such as —C≡C—$CH_3$. The term "cycloalkyl" refers to a saturated, cyclic hydrocarbon moiety, such as cyclohexyl. The term "cycloalkenyl" refers to a non-aromatic, cyclic hydrocarbon moiety that contains at least one double bond, such as cyclohexenyl. The term "heterocycloalkyl" refers to a saturated, cyclic moiety having at least one ring heteroatom (e.g., N, O, or S), such as 4-tetrahydropyranyl. The term "heterocycloalkenyl" refers to a non-aromatic, cyclic moiety having at least one ring heteroatom (e.g., N, O, or S) and at least one ring double bond, such as pyranyl. The term "aryl" refers to a hydrocarbon moiety having one or more aromatic rings. Examples of aryl moieties include phenyl (Ph), phenylene, naphthyl, naphthylene, pyrenyl, anthryl, and phenanthryl. The term "heteroaryl" refers to a moiety having one or more aromatic rings that contain at least one heteroatom (e.g., N, O, or S). Examples of heteroaryl moieties include furyl, furylene, fluorenyl, pyrrolyl, thienyl, oxazolyl, imidazolyl, thiazolyl, pyridinyl, pyrimidinyl, quinazolinyl, quinolyl, isoquinolyl and indolyl.

In some embodiments, A is a five-membered ring optionally substituted with 1-3 substituents (such as those defined in $R_{13}$, $R_{14}$, and $R_{15}$ described below).

In some embodiments, each of $R_5$, $R_6$, $R_7$, $R_8$, $R_9$, $R_{10}$, $R_{11}$, and $R_{12}$ is H.

In some embodiments, a compound of formula (I) is a compound of formula (Ia):

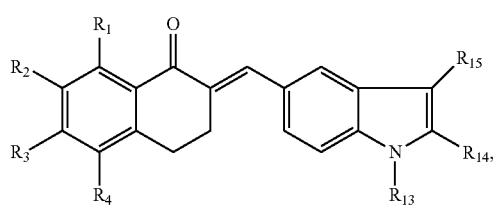

(Ia)

in which each of $R_1$, $R_2$, $R_3$, and $R_4$ is defined above; and each of $R_{13}$, $R_{14}$, and $R_{15}$, independently, is H, halo, CN, OR", COOR", C(O)R", $C_1$-$C_{10}$ alkyl, $C_1$-$C_{10}$ arylalkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl; R" being H, $C_1$-$C_{10}$ alkyl, $C_3$-$C_{20}$ cycloalkyl, $C_3$-$C_{20}$ heterocycloalkyl, aryl, or heteroaryl. In such embodiments, $R_2$ can be H, F, Br, or $CH_3O$; $R_3$ can be H or $CH_3O$; and $R_{13}$ can be H, $CH_3$, $C_2H_5$, $CH_2Ph$, $CH_3O$, $C(O)CH_3$, or $COO(t\text{-butyl})$. Exemplary compounds of formula (Ia) include Compounds 1-3, 5-14, 16, 17, 19, 20, and 22 described in Table 1.

In some embodiments, a compound of formula (I) is a compound of formula (Ib):

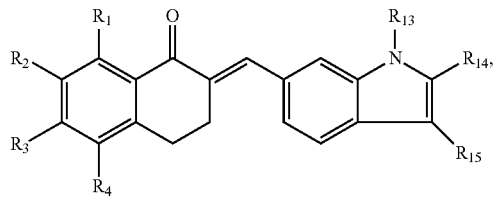

(Ib)

in which each of $R_1$, $R_2$, $R_3$, and $R_4$ is defined above; and each of $R_{13}$, $R_{14}$, and $R_{15}$, independently, is H, halo, CN, OR", COOR", C(O)R", $C_1$-$C_{10}$ alkyl, $C_1$-$C_{10}$ arylalkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl; R" being H, $C_1$-$C_{10}$ alkyl, $C_3$-$C_{20}$ cycloalkyl, $C_3$-$C_{20}$ heterocycloalkyl, aryl, or heteroaryl. In such embodiments, $R_2$ can be H, Br, or $CH_3O$; $R_3$ can be H or $CH_3O$; and $R_{13}$ can be $CH_3$. Exemplary compounds of formula (Ib) include Compounds 4, 15, 18, and 21 described in Table 1.

Exemplary compounds of formula (I) include Compounds 1-22 listed in Table 1 below. Exemplary Compounds 1-22 are those of formula (Ia) or (Ib), in which $R_1$, $R_2$, $R_3$, $R_4$, $R_{13}$, $R_{14}$, and $R_{15}$ are those shown in Table 1.

TABLE 1

| Compound No. | Formula | $R_1$ | $R_2$ | $R_3$ | $R_4$ | $R_{13}$ | $R_{14}$ | $R_{15}$ |
|---|---|---|---|---|---|---|---|---|
| 1 | Ia | H | H | H | H | H | H | H |
| 2 | Ia | H | H | H | H | $CH_3$ | H | H |
| 3 | Ia | H | H | H | H | $C_2H_5$ | H | H |
| 4 | Ib | H | H | H | H | $CH_3$ | H | H |
| 5 | Ia | H | H | H | H | t-butoxycarbonyl | H | H |
| 6 | Ia | H | F | H | H | $CH_3$ | H | H |
| 7 | Ia | H | F | H | H | H | H | H |
| 8 | Ia | H | F | H | H | $C_2H_5$ | H | H |
| 9 | Ia | H | F | H | H | $CH_3CO$ | H | H |
| 10 | Ia | H | F | H | H | t-butoxycarbonyl | H | H |
| 11 | Ia | H | F | H | H | benzyl | H | H |
| 12 | Ia | H | $CH_3O$ | H | H | $C_2H_5$ | H | H |
| 13 | Ia | H | $CH_3O$ | H | H | H | H | H |
| 14 | Ia | H | $CH_3O$ | H | H | $CH_3$ | H | H |
| 15 | Ib | H | $CH_3O$ | H | H | $CH_3$ | H | H |
| 16 | Ia | H | $CH_3O$ | $CH_3O$ | H | $CH_3$ | H | H |
| 17 | Ia | H | $CH_3O$ | $CH_3O$ | H | $C_2H_5$ | H | H |
| 18 | Ib | H | $CH_3O$ | $CH_3O$ | H | $CH_3$ | H | H |
| 19 | Ia | H | Br | H | H | H | H | H |
| 20 | Ia | H | Br | H | H | $CH_3$ | H | H |
| 21 | Ib | H | Br | H | H | $CH_3$ | H | H |
| 22 | Ia | H | Br | H | H | $C_2H_5$ | H | H |

The compounds of formula (I) can be made by methods known in the art or methods described herein. Examples 1-4 below provide detailed descriptions of how compounds 1-22 were actually prepared.

Scheme I shown below illustrates a typical synthetic route for synthesizing exemplary compounds 1-22 described herein.

Scheme 1

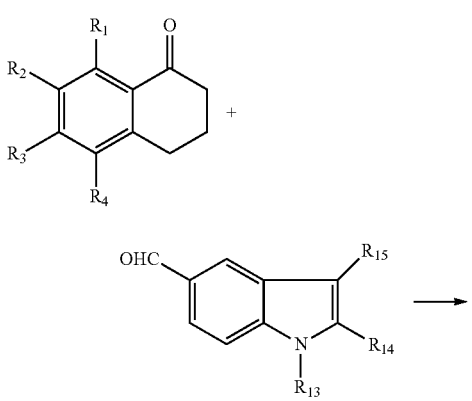

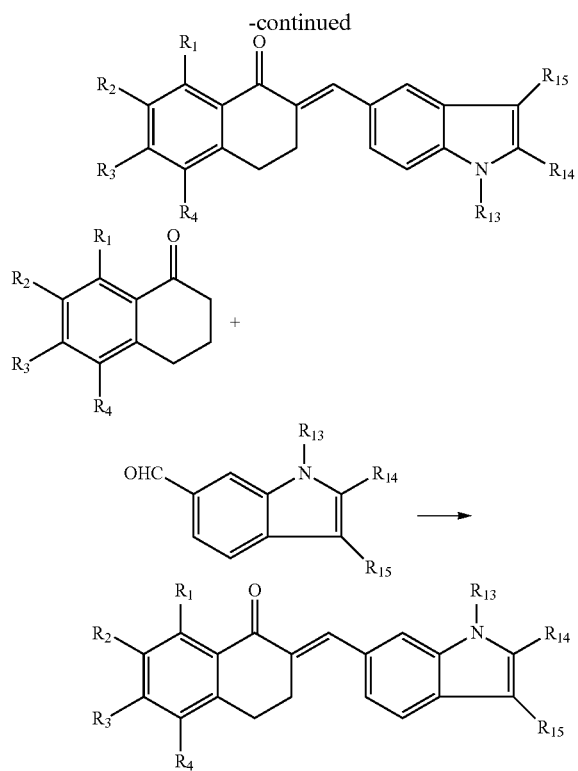

In Scheme I, $R_1$, $R_2$, $R_3$, $R_4$, $R_{13}$, $R_{14}$, and $R_{15}$ can be those defined above. As shown in Scheme I, a chalcone compound can be synthesized by reacting a tetralone compound with an aldehyde (e.g., an aldehyde containing an indole group) through an aldo condensation reaction. Other chalcone compounds of formula (I) can be prepared in a similar manner. The synthesized chalcone compound can then be purified by a suitable method such as column chromatography, high-pressure liquid chromatography, or recrystallization.

The chalcone compounds mentioned herein may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

This disclosure also features pharmaceutical compositions containing a therapeutically effective amount of at least one (e.g., two or more) of the chalcone compounds described herein (i.e., the compounds of formula (I)) or a salt thereof (e.g., a pharmaceutically acceptable salt thereof) as an active ingredient, as well as at least one pharmaceutically acceptable carrier (e.g., adjuvant or diluent). Examples of pharmaceutically acceptable salts include acid addition salts, e.g., salts formed by reaction between a compound of formula (I) and hydrohalogen acids (such as hydrochloric acid or hydrobromic acid), mineral acids (such as sulfuric acid, phosphoric acid and nitric acid), and aliphatic, alicyclic, aromatic or heterocyclic sulfonic or carboxylic acids (such as formic acid, acetic acid, propionic acid, succinic acid, glycolic acid, lactic acid, malic acid, tartaric acid, citric acid, benzoic acid, ascorbic acid, maleic acid, hydroxymaleic acid, pyruvic acid, p-hydroxybenzoic acid, embonic acid, methanesulphonic acid, ethanesulphonic acid, hydroxyethanesulphonic acid, halobenzenesulphonic acid, trifluoroacetic acid, trifluoromethanesulphonic acid, toluenesulphonic acid, and naphthalenesulphonic acid).

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical carriers for delivery of an active chalcone compound described herein. Examples of other carriers include colloidal silicon oxide, magnesium stearate, cellulose, sodium lauryl sulfate, and D&C Yellow #10.

The pharmaceutical composition described herein can optionally include at least one further additive selected from a disintegrating agent, binder, lubricant, flavoring agent, preservative, colorant and any mixture thereof. Examples of such and other additives can be found in "Handbook of Pharmaceutical Excipients"; Ed. A. H. Kibbe, 3rd Ed., American Pharmaceutical Association, USA and Pharmaceutical Press UK, 2000.

The pharmaceutical composition described herein can be adapted for parenteral, oral, topical, nasal, rectal, buccal, or sublingual administration or for administration via the respiratory tract, e.g., in the form of an aerosol or an air-suspended fine powder. The term "parenteral" as used herein refers to subcutaneous, intracutaneous, intravenous, intramuscular, intraarticular, intraarterial, intrasynovial, intrasternal, intrathecal, intralesional, intraperitoneal, intraocular, intra-aural, or intracranial injection, as well as any suitable infusion technique. In some embodiments, the composition can be in the form of tablets, capsules, powders, microparticles, granules, syrups, suspensions, solutions, nasal spray, transdermal patches, injectable solutions, or suppositories.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art.

A composition having one or more active chalcone compounds can also be administered in the form of suppositories for rectal administration.

In addition, this disclosure features a method of using a chalcone compound as outlined above for treating cancer or for the manufacture of a medicament for such a treatment. The method can include administering to a patient in need thereof the pharmaceutical composition described herein in an amount effective to treat the cancer. Exemplary cancers that can be treated by the chalcone compounds disclosed herein include breast, stomach, lung, colorectal, prostate, liver, ovarian, uterine, pancreatic, rectum, mouth, esophagus, cervical, testicular, bladder, skin, bone, kidney, brain, head and neck, and throat cancers, as well as leukemia, sarcoma, choriocarcinoma, and lymphoma. "An effective amount" refers to the amount of the pharmaceutical composition that is required to confer a therapeutic effect on the treated subject.

As used herein, the terms "treatment," "treat," and "treating" refer to reversing, alleviating, delaying the onset of, or inhibiting the progress of, a cancer or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The typical dosage of the chalcone compounds described herein can vary within a wide range and will depend on various factors, such as the types of diseases treated, the individual needs of each patient, route of administration, excipient usage, and the possibility of co-usage with other therapeutic treatment. Exemplary daily dosages can be at least about 0.1 mg (e.g., at least about 0.5 mg, at least about 1 mg, at least about 5 mg, at least about 10 mg, at least about 15 mg, at least about 20 mg, at least about 50 mg, or at least about 100 mg) and/or at most about 500 mg (e.g., at most about 400 mg, at most about 300 mg, at most about 200 mg, at most about 100 mg, at most about 75 mg, at most about 50 mg, at most about 20 mg, or at most about 15 mg) of a chalcone compound. The skilled person or physician may consider relevant variations to this dosage range and practical implementations to accommodate the situation at hand.

In some embodiments, the pharmaceutical composition described herein can be administered once daily. In some embodiments, the pharmaceutical composition can be administered more than once daily (e.g., twice daily, three times daily, or four times daily).

The present disclosure also features a method of destabilizing microtubules in a cell (e.g., in a patient body or in a tissue sample obtained from a patient). The method includes contacting the cell with a chalcone compound described herein in an amount sufficient to destabilize the microtubules in the cell. Without wishing to be bound by theory, it is believed that the chalcone compounds described herein can destabilize microtubules (e.g., by depolymerizing α-tubulin polymers in microtubules) during cancer cell division, thereby leading to mitotic arrest and ultimately to cancer cell death.

In addition, the present disclosure features a method of modulating ASK1 or stathmin activity in a cell (e.g., in a patient body or in a tissue sample obtained from a patient). The method includes contacting the cell with a chalcone compound described herein. Without wishing to be bound by theory, it is believed that the chalcone compounds described herein can modulate the activities of ASK-1 and/or its downstream target stathmin to decrease the levels of α-tubulin monomers available for polymerization and/or promote disassembly of existing microtubules.

The contents of all publications cited herein (e.g., patents, patent application publications, and articles) are hereby incorporated by reference in their entirety.

The following examples are illustrative and not intended to be limiting.

EXAMPLES

All reagents and solvents were purchased from commercial vendors and used without purification. NMR was recorded on a Varian 400 MHz NMR equipped with 5 mm AutoX OneProbe in the Harvard Medical School East Quart NMR facility.

Molecular mass was determined on an Agilent 1100 HPLC with ABI 2000 MS/MS mass spectrometer.

Example 1

Synthesis of (2E)-7-fluoro-2-[(1-methyl-1H-indol-5-yl)methylidene]-1,2,3,4-tetrahydronaphthalen-1-one (Compound 6)

Sodium hydroxide (8 M, 0.6 mL) was added to a mixture of 7-fluoro-1-tetralone (82 mg, 0.5 mmol) and N-methylindole-5-carbaldehyde (80 mg, 0.5 mmol) in three (3) mL of EtOH and stirred at room temperature overnight. The resulting precipitate was collected via filtration, and washed with EtOH and water to yield Compound 6 as a fine yellow solid in 90% yield.

$^1$H NMR (400 MHz, DMSO-$d_6$): δ 2.91-2.95 (m, 2H), 3.17-3.20 (m, 2H), 3.28 (s, 3H), 6.52 (d, J=3.2 Hz, 1H), 7.36-7.44 (m, 4H), 7.52 (d, J=8.8 Hz, 1H), 7.63 (dd, J=8.8, 1.6 Hz, 1H), 7.80 (s, 1H), 7.90 (s, 1H). ESI(+)—MS m/z calc'd for $C_{20}H_{16}FNO$: 305.35; found: 307.3 $(M+2H)^+$, 612.7 $(2M+2H)^{2+}$.

Example 2

Synthesis of (2E)-7-fluoro-2-(1H-indol-5-ylmethylidene)-1,2,3,4-tetrahydronaphthalen-1-one (Compound 7)

Sodium hydroxide (8 M, 0.6 mL) was added to a mixture of 7-fluoro-1-tetralone (82 mg, 0.5 mmol) and indole-5-carboxaldehyde (73 mg, 0.5 mmol) in three (3) mL of EtOH and stirred at room temperature overnight. The resulting precipitate was collected via filtration, and washed with EtOH and water to yield Compound 7 as a fine orange solid.

$^1$H NMR (400 MHz, DMSO-$d_6$): δ 2.92-2.95 (m, 2H), 3.18-3.21 (m, 2H), 6.52 (s, 1H), 7.31 (d, J=1.6 Hz, 1H), 7.41-7.49 (m, 4H), 7.64 (dd, J=8.8, 2.4 Hz, 1H), 7.81 (s, 1H), 7.89 (s, 1H), 11.31 (br s, 1H). ESI(+)—MS m/z calc'd for $C_{19}H_{14}FNO$: 291.33; found: 293.3 $(M+2H)^+$, 584.6 $(2M+2H)^{2+}$.

Example 3

Synthesis of (2E)-2-[(1-ethyl-1H-indol-5-yl)methyl-idene]-7-fluoro-1,2,3,4-tetrahydronaphthalen-1-one (Compound 8)

Sodium hydroxide (8 M, 0.6 mL) was added to a mixture of 7-fluoro-1-tetralone (82 mg, 0.5 mmol) and N-ethyl-indole-5-carbaldehyde (85 mg, 0.5 mmol) in three (3) mL of EtOH and stirred at room temperature overnight. The resulting precipitate was collected via filtration, and washed with EtOH and water to yield Compound 8 as a fine yellow solid.

$^1$H NMR (400 MHz, DMSO-$d_6$): δ 1.37 (t, J=6.4 Hz, 3H), 2.91-2.95 (m, 2H), 2.91-2.95 (m, 2H), 4.24 (q, J=6.4 Hz, 2H), 6.52 (d, J=3.2 Hz, 1H), 7.35 (d, J=8.4, 1.6 Hz, 1H), 7.37 (m, 3H), 7.56-7.58 (d, J=8.4 Hz, 1H), 7.63 (d, J=8.8, 2.4 Hz, 1H), 7.82 (s, 1H), 7.95 (s, 1H). ESI(+)—MS m/z calc'd for $C_{21}H_{18}FNO$: 319.38; found: 321.3 $(M+2H)^+$, 640.8 $(2M+2H)^{2+}$.

Example 4

Synthesis of Compounds 1-5 and 9-22

Compounds 1-5 and 9-22 were synthesized by the method described in Example 1 using appropriate starting materials.

Example 5

Biological Assays

Compounds 1-22 synthesized in Examples 1-4 were characterized by $^1$H NMR and mass spectra. The purity of these compounds was more than 90% as measured by reverse phase HPLC analyses. These compounds were diluted in DMSO at 25 mM and then diluted in culture medium at 0.001-10 µM final concentrations. All compounds were soluble and did not precipitate in the medium. These compounds were subsequently tested in one or more assays described below.

Cell Culture

PC3 (provided by Dr. Steven Balk's laboratory in Department of Medicine at Beth Israel Deaconess Medical Center), PANC02 and CRL2119 (provided by Dr. Pankaja Seth's laboratory in Department of Medicine at Beth Israel Deaconess Medical Center), A549 (ATCC) cell lines were cultured according to manufacturer's protocols. Briefly, PC3 were cultured in RPMI medium supplemented with 10% FBS (Atlanta). PANC-2, A549 and CRL2119 were cultured in DMEM High medium supplemented with 10% FBS (Atlanta). Human bronchial epithelial cells (BEC) were cultured in Airway Epithelial Cell Basal Medium with the Bronchial Epithelial cell growth kit (ATCC) according to manufacturer's protocol and used at passages 3-5.

Crystal Violet Staining

Cells were seeded at $5 \times 10^3$ concentration in 96 well plates and treated with test compounds or DMSO (0.001-10 µM) for 72 hours. Culture medium was removed and cells were stained with crystal violet solution (Sigma-Aldrich) for 15 minutes while shaking at room temperature. Crystal violet was then removed and cells were repeatedly washed in water. Attached cells stained with crystal violet were dried and then resuspended in 10% acetic acid. Absorbance was measured at 562 nm. The intensity of staining corresponded directly to the number of live cells.

Annexin V Staining

PC3 cells were seeded at $1 \times 10^5$ concentration in 6 well plates 24 hours before experiment. Cells were treated with Compound 6 for 24 hours. Cells were harvested and apoptosis rate was measured using Annexin V-FITC staining according to manufacturer's protocol (BD Biosciences, San Jose, Calif.).

Immunostaining

Immunofluorescence and immunostaining on cell lines and tumor samples were performed as described in Wegiel et al, *Cancer research* 2013, 73(23), 7009-21. Anti-mouse STMN1, anti-P (Ser10)-Histone H3, and α-tubulin antibody were obtained from Cell Signaling. β-actin antibody was obtained from Sigma-Aldrich. Cells were treated with Compound 6 (1 µM) or DMSO for 48 hours. After immunofluorescence staining, the number of P-Histone H3 was quantified per field of view at 40× magnification using Zeiss Axiovert Microscope.

Immunoblotting and Immunoprecipitation

Snap-frozen tissue samples were homogenized in ice-cold tissue lysis buffer (250 mM NaCl, 5 mM EDTA, 1% Triton X-100, 10 mM Tris-HCl; pH 7.5) containing the protease inhibitor cocktail Complete Mini (Roche). For co-immunoprecipitation, 200 µg protein lysates in RIPA buffer and the protease inhibitor cocktail were mixed with appropriate antibodies and 30 µl Protein A/G Plus-agarose beads (Santa Cruz Biotechnology) and then rotated for 1 hour at room temperature. The proteins were washed with RIPA buffer and eluted (95° C., 5 min in SDS loading buffer). Immunoblotting was performed as previously described in Chin et al., *Proc. Natl. Acad. Sci. USA* 2007, 104(12), 5109-14. Antibodies: P (Ser967)-ASK1 (Cell Signaling), Ask1 (Cell Signaling), P-STMN1 (Ser16) (Cell Signaling), STMN1 (Cell Signaling), 13-Actin (Sigma) were used at 1:1000 dilution.

Mitosox ROS Assay

MitoSox Red mitochondrial superoxide indicator was used to measure reactive oxygen species (ROS) generation in PC3 treated with test compounds. Briefly, PC3 cells were treated with test compounds for 30 minutes and loaded with 5 µM MitoSox solution and incubated for 10 min in dark at 37° C. Cells were harvested immediately and fluorescence was measured by flow cytometry.

Transfection with siRNA siRNA against STMN1 and scramble siRNA were obtained from Darmacon (ONTARGET plus siRNA). PC3 cells were transiently transfected with siRNA against STMN1 or scramble siRNA using Lipofectamine 2000 (Invitrogen) as previously described in Wegiel et al., *J. Biol. Chem.* 2009, 7; 284(32):21369-78. Twenty four hours post-transfection, cells were split to 96 well plates and treated with test compounds for 72 hours. STMN1 levels were measured by immunoblotting to confirm successful knockdown.

Invasion Chambers

The invasion of A549 cells was measured using Transwell chambers (Chemicon, Millipore, Calif.) according to the manufacturer's protocol. Briefly, A549 cells were treated with test compounds at 1 µM in 500 µl of DMEM medium without FBS for 24 hours. Medium in the upper chamber was serum-free while medium in the lower chamber contained 10% FBS as a source of chemoattractants. Cells that passed through the Matrigel-coated membrane were stained and photographed after 24 hours of incubation. Absorbance was measured at 562 nm by ELISA reader after dissolving of stained cells in 10% acetic acid.

RT² Profiler PCR Array and Geo Profiles

RT² profiler PCR array Human Cancer Pathway was purchased from SA Biosciences. RNA from PC3 cells treated with DMSO or Compound 6 were isolated and prepared for RT-PCR following manufacturer' protocol. Analysis was performed online using the software provided by SA Biosciences. The upregulated genes were further confirmed using real time PCR.

GEO profiles from 18 normal prostatic tissues (without any pathological alterations), 62 tissues adjacent to tumors, 64 primary tumors and 24 metastatic samples were obtained from patients with prostate cancer as described in Chandran et al., *BMC cancer* 2007, 7:64. Specifically, 24 metastatic biopsies were derived from 4 patients with prostate cancer metastases to the liver, lymph nodes, kidney, lung and adrenal glands. STMN1 and ASK1 expressions were analyzed.

In Silico Evaluation of Interactions Between ASK1 Protein and Chalcone Compounds Molecular modeling and docking analyses were preformed on custom-assembled computer systems containing dual Intel Xeon processors (48 threads at 2.6 GHz), three Nvidia Geforce GTX Titan X GPUs (9216 CUDA cores at 1075 MHz), and a 1 TB PCI-E SSHD or containing an Intel Xeon processor (16 threads at 3.9 GHz) with an Nvidia Geforce GTX Titan Black GPU (2880 cores at 980 MHz). Test compounds and ASK1 protein structures were prepared for docking and results were visualized using AutoDock-Tools as described in Morris et al., *Journal of Computational Chemistry* 2009, 30(16), 2785-91. Docking of Compound 6 was preformed using Autodock Vina as described in Trott et al., *Journal of Computational Chemistry* 2010, 31(2), 455-61 to the full protein structure of ASK1 (PDB: 2CLQ) to generate the lowest energy binding pose.

Statistical Analyses

Statistical analyses were performed using GraphPad Prism. Data were presented as the mean±SD and were representative for at least three independent experiments. ANOVA or Student T test was used for estimation of statistical significance for the experiments (p<0.05).

Results:

Chalcone Compounds Induced Cell Death in Cancer Cells.

The cytoxicity of Compounds 1-22 against A549 and PC3 cell lines are summarized in Table 2 below.

TABLE 2

| Compound | Cytoxicity (% cell killing at 10 μM)[a] | |
|---|---|---|
| No. | A549 | PC3 |
| 1 | 47 | 55 |
| 2 | 56 | 52 |
| 3 | 52 | 58 |
| 4 | 53 | 61 |
| 5 | N.A.[b] | N.A. |
| 6 | 47 | 49 |
| 7 | 43 | 45 |
| 8 | 38 | 33 |
| 9 | 28 | 24 |
| 10 | N.A. | N.A. |
| 11 | N.A. | N.A. |
| 12 | 20 | 49 |
| 13 | 5 | 55 |
| 14 | 21 | 18 |
| 15 | 24 | 42 |
| 16 | N.A. | 31 |
| 17 | 19 | 45 |
| 18 | 41 | 55 |
| 19 | 16 | 42 |

TABLE 2-continued

| Compound | Cytoxicity (% cell killing at 10 μM)[a] | |
|---|---|---|
| No. | A549 | PC3 |
| 20 | 21 | 47 |
| 21 | 26 | 39 |
| 22 | N.A. | N.A. |

Figure 1E:
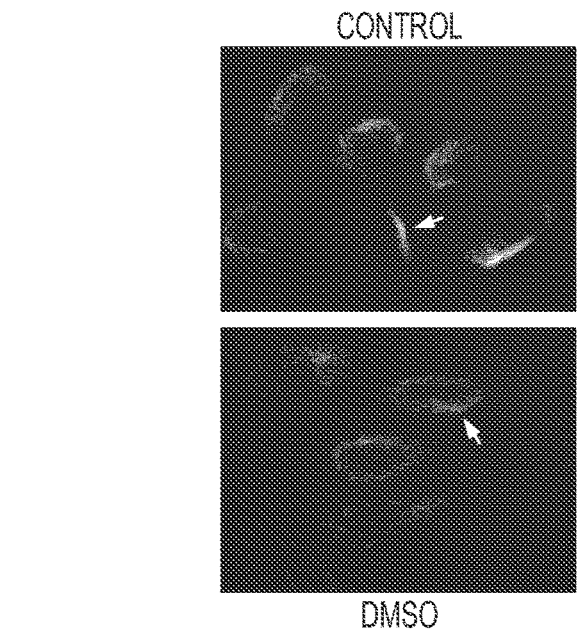
Figure 1E:
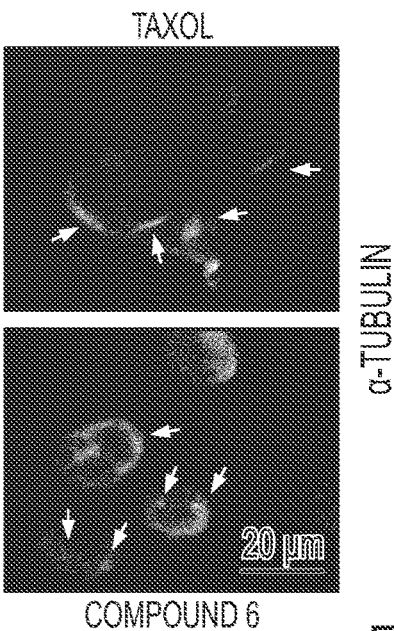

[a]average of triplicates, % of apoptotic cells in treatment groups as compared to DMSO controls,
[b]N.A.: not active at 10 μM To further evaluate the efficacy of Compound 6, the following four cancer cell lines were used: PC3 (prostate cancer), A549 (lung cancer), CLR2119 and PAN02 (pancreatic cancer). Compound 6 was tested in the 0.01-10 μM concentrations range. FIGS. 1A-1D show that Compound 6 strongly decreased survival of cancer cells with IC50 at 0.14-0.3 μM dependently on cell type (FIGS. 1A-D) and with the highest efficiency in PC3 cells (FIG. 1A). Compound 6 did not inhibit DNA synthesis as tested by BrDU proliferation (data not shown), yet it showed significant effect on microtubule stability. FIG. 1E shows the comparative results between the effects of Compound 6 and the effects of the well-known microtubule-stabilizing agent docetaxel in PC3 cells on microtubule stability. As shown in FIG. 1E, in contrast to stabilization of microtubules upon treatment with docetaxel, Compound 6 suppressed mitotic spindle formation, as well as accumulation of α-tubulin and microtubules in PC3 cells. This data suggest that Compound 6 destabilizes microtubules and mitotic spindle formation. Further, FIG. 1F shows that Compound 6 disintegrated β-actin microfilament cytoskeleton, likely due to mitotic catastrophe or apoptosis. Importantly, FIG. 1G shows that treatment of PC3 cells with Compound 6 led to increased number of Annexin V-positive cells, suggesting induction of early apoptosis.

Chalcone Compounds were Efficient in Inducing Cancer Cell Death

FIGS. 2A and 2B show that Compounds 7 and 8 were similarly efficient in inducing cancer cell death in PC3 and A549 cell lines compared to Compound 6. Among these three compounds, Compound 8 (in which the indole group is substituted with —CH₂CH₃ on the nitrogen atom) appeared to be the most efficient as compare to Compound 6 (in which the indole group is substituted with —CH₃ on the nitrogen atom) and Compound 7 (in which the indole group is unsubstituted). FIGS. 2A and 2B also show that A549 and PC3 cells were similarly blocked in growth with significant cell death after treatment with these three chalcone compounds.

STMN1 is a Target of Chalcone Compounds

Figure 2C:
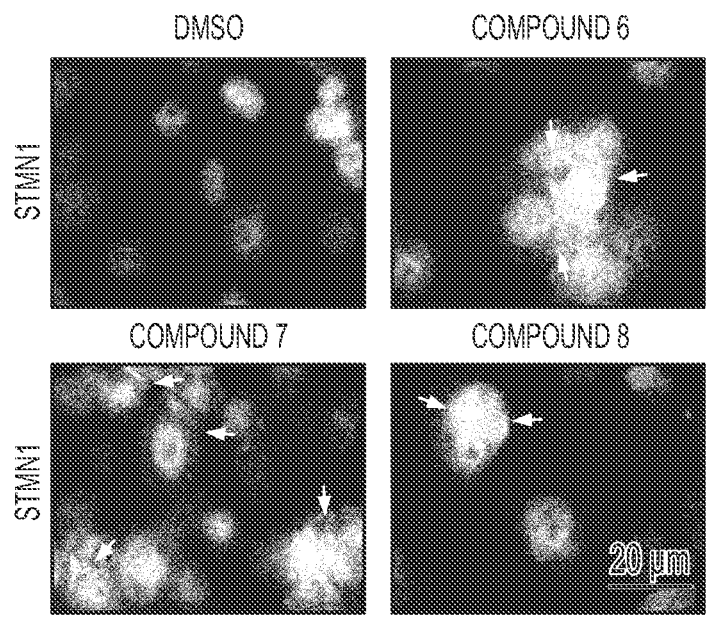
FIG. 2C are images showing STMN1 immunostaining in PC3 cells treated with Compounds 6-8 for 24 hours.
Figure 2D:
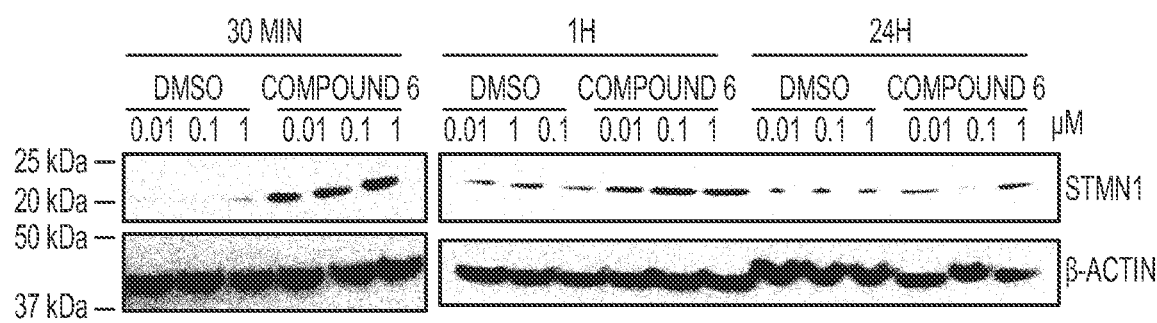
FIG. 2D are images of immunoblotting with antibody against STMN1, P—Rb (G1/S transition marker), cyclin B 1 (G2/M marker), and β-Actin in PC3 cells treated with 0.01, 0.1, and 1 μM Compound 6 for 30 minutes, 1 hour, and 24 hours (n=3).
Figure 2E:
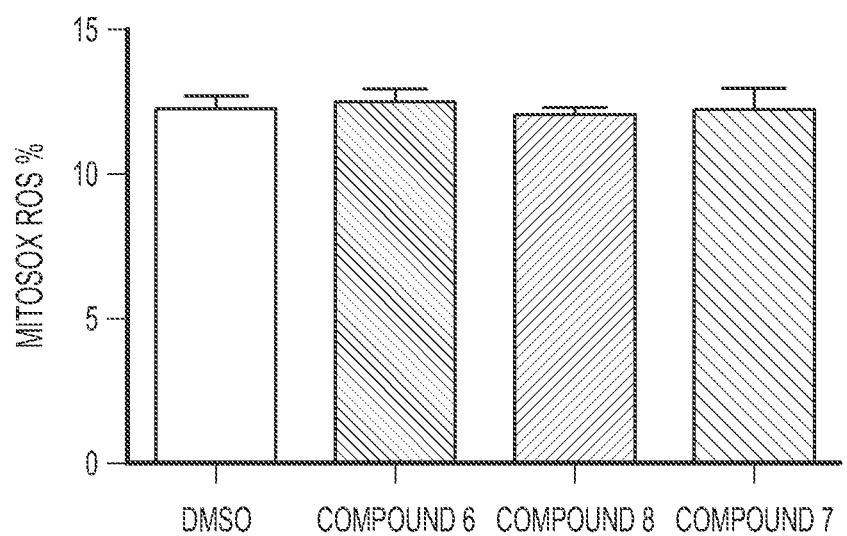
FIG. 2E is a graph showing that Mitosox ROS assay results obtained from Compounds 6-8.

As the above results show that Compound 6 treatment led to destabilization of microtubules, it is believed that mitotic catastrophe is a part of the mechanism behind the effects of the chalcone compounds described herein in cancer cell lines. RT2 profiler PCR array was used to identify specific pathways that were affected by Compound 6. mRNA of two genes were found elevated more than 4 fold after treatment: adrenomedullin and stathmin (STMN1). Since STMN1 is major mitotic regulator and was affected by the chalcone compounds in vitro, the effects of the chalcone compounds on this target were further studied. FIG. 2C shows that accumulation of STMN1 in cells after treatment with Compound 6-8 by immunofluorescence. Further, FIG. 2D shows very early (30 minutes to 1 hour) stabilization of STMN1 in PC3 cells treated with Compound 6 by immunoblotting, but with the levels of STMN1 decreasing to the baseline at 24 hours. Importantly, none of Compounds 6-8 increased ROS levels (FIG. 2E) or influenced mitochondria activity as measured by MTT assay (data not shown), suggesting an oxidative-stress-independent mechanism of action.

STAIMN1 Activity is Modulated by Chalcone Compounds In Vitro

Figure 3A:
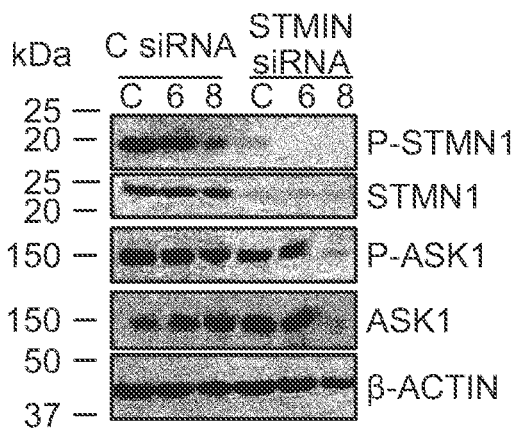
FIG. 3A are images of immunoblotting with antibody against STMN1 in PC3 cells transiently transfected with siRNA against STMN1 or control siRNA. Efficiency of transfection was tested after 48 hours and additional 24 hours after treated with 1 μM Compound 6.
Figure 3B:
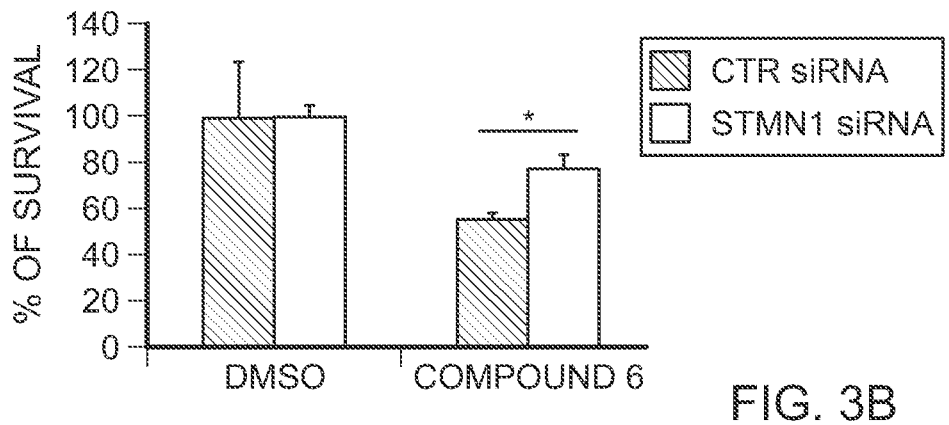
FIGS. 3B-3D are graphs showing crystal violet staining of PC3 cells transfected with siRNA against STMN1 or control siRNA for 48 hours and treated with 1 μM Compound 6, 1 μM Compound 7, and 0.1 μM Compound 8 for 72 hours (n=4, *p<0.05, **p<0.01).
Figure 3C:
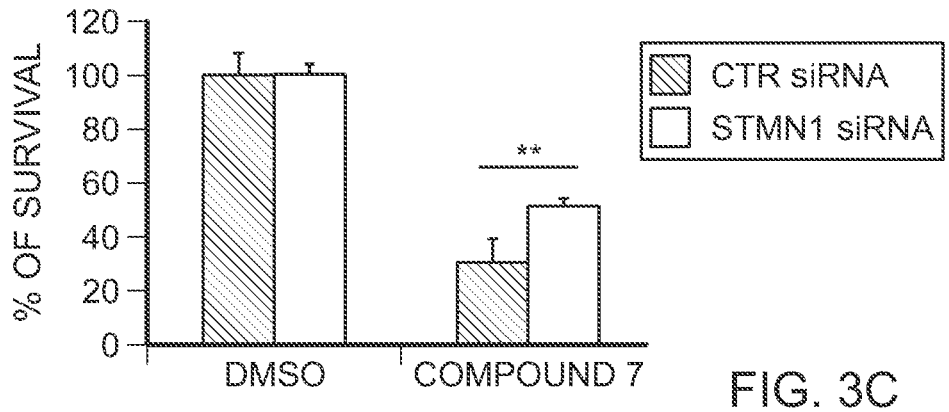
Figure 3D:
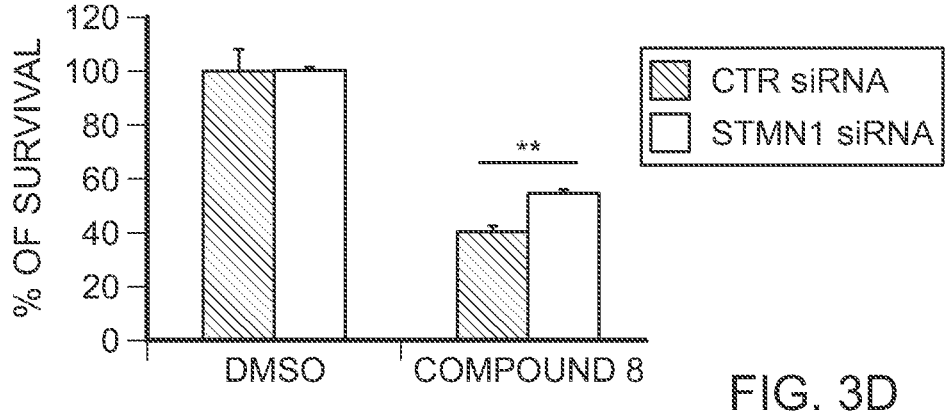
Figure 3E:
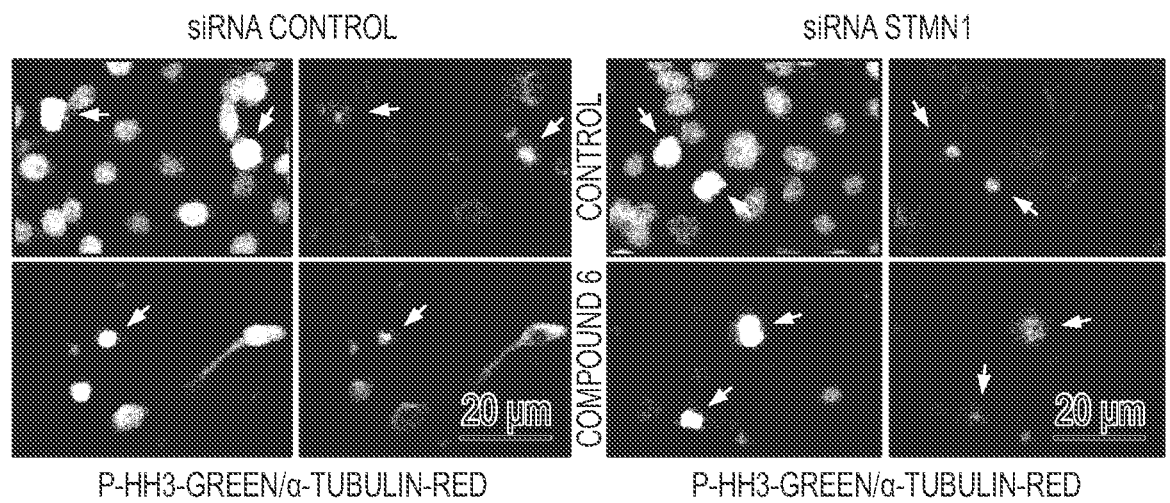
FIG. 3E are images of immunofluorescence staining with antibody against P-HH3 (green) and α-tubulin (red) in PC3 cells transfected with siRNA against STMN1 or control siRNA and treated with 1 μM Compound 6. Arrows indicate mitotic cells.
Figure 3F:
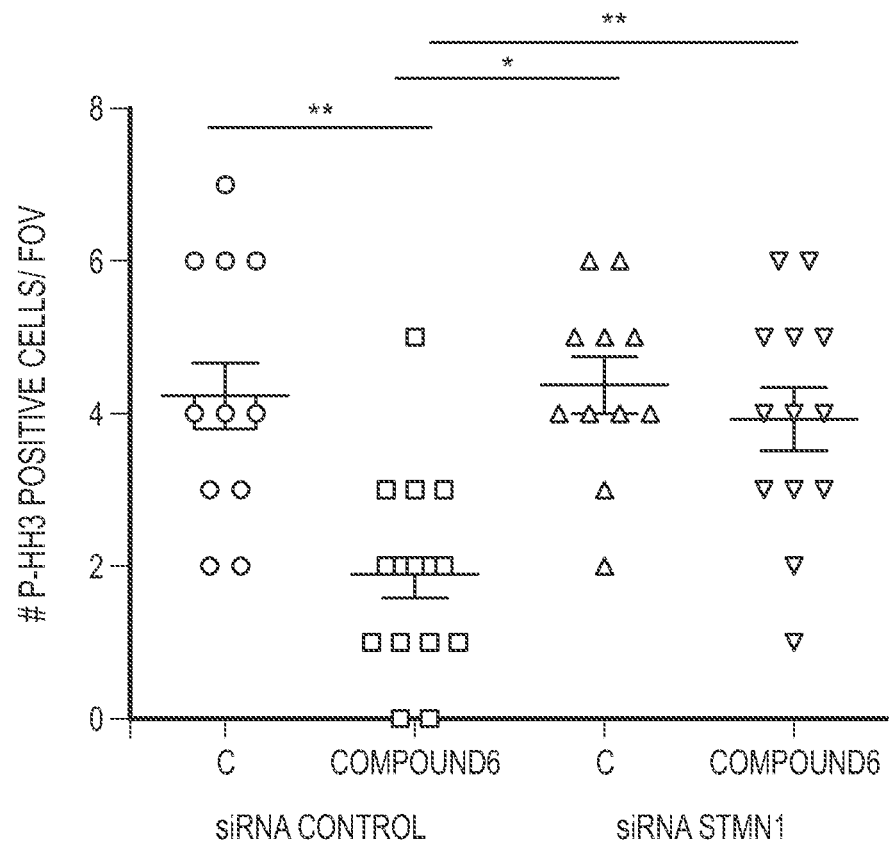
FIG. 3F is a graph showing the number of P-HH3 per field of view (FOV) in PC3 cells transfected with siRNA against STMN1 or control siRNA and treated with 1 μM Compound 6 (p<0.05).

To evaluate the role of STMN1 in mediating anti-tumor effects of chalcone compounds, siRNA was employed against STMN1 in PC3 cells. FIG. 3A shows successful deletion of STMN1 in PC3 cells 48 hours post-transfection with siRNA against STMN1 in both untreated and Compound 6 treated cells. FIG. 3B shows that accelerated cell death in response to Compound 6 was attenuated in the absence of STMN1. FIGS. 3C and 3D show similar observation in PC3 cells transfected with siRNA against STMN1 and treated with Compound 7 or Compound 8. Further, experiments were conducted to assess whether decreased levels of STMN1 in PC3 cells transfected with siRNA against STMN1 influenced Compound 6-mediated microtubule destabilization during mitosis. FIGS. 3E and 3F show that Compound 6 blocked number of cells undergoing mitosis (P-Histone H3) and those presented with normal mitotic spindles (α-tubulin). FIGS. 3E and 3F also show that microtubule destabilization and aberrant mitotic spindle as well as number of P-Histone H3 positive cells in response to Compound 6 were in part reversed in the absence of STMN1, suggesting that STMN1 may be one of the critical targets for Compound 6 and responsible in part for the effects of the chalcone compounds in PC3 cells.

Expression of STMN1 in Cancer Biopsies

Figure 4A:
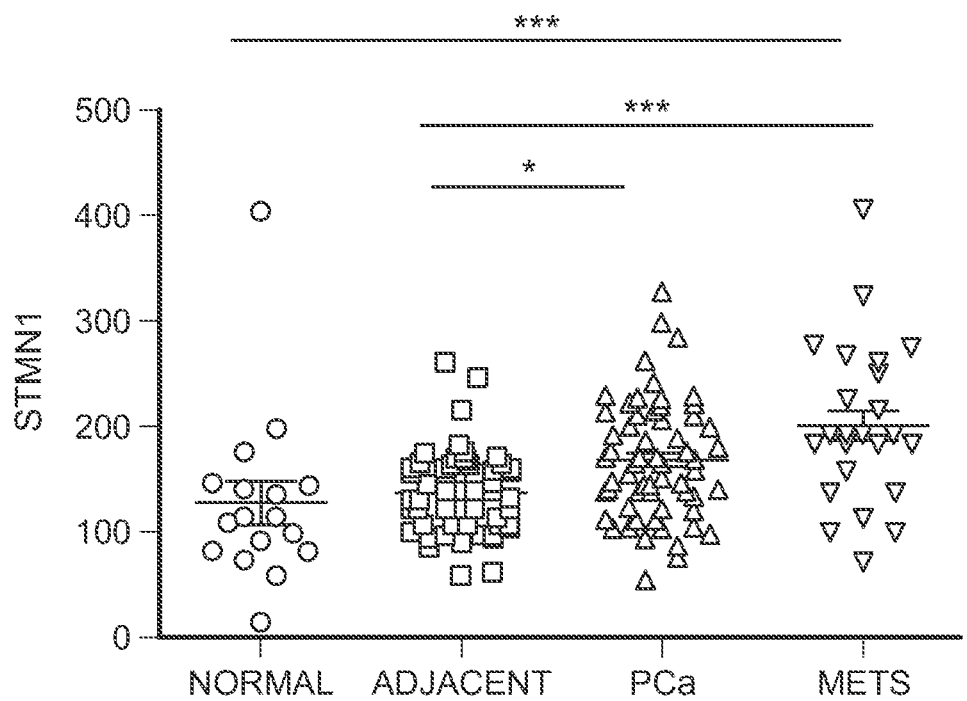
FIGS. 4A and 4B are graphs showing high STMN1 and ASK1 mRNA levels in patient samples from advanced and metastatic prostate cancer.
Figure 4B:
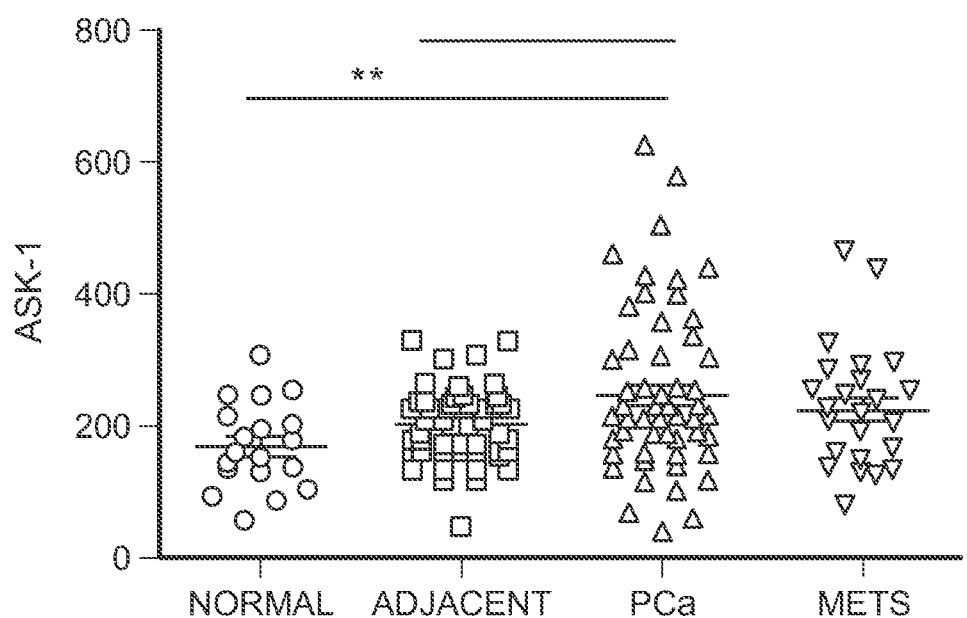
Figure 4C:
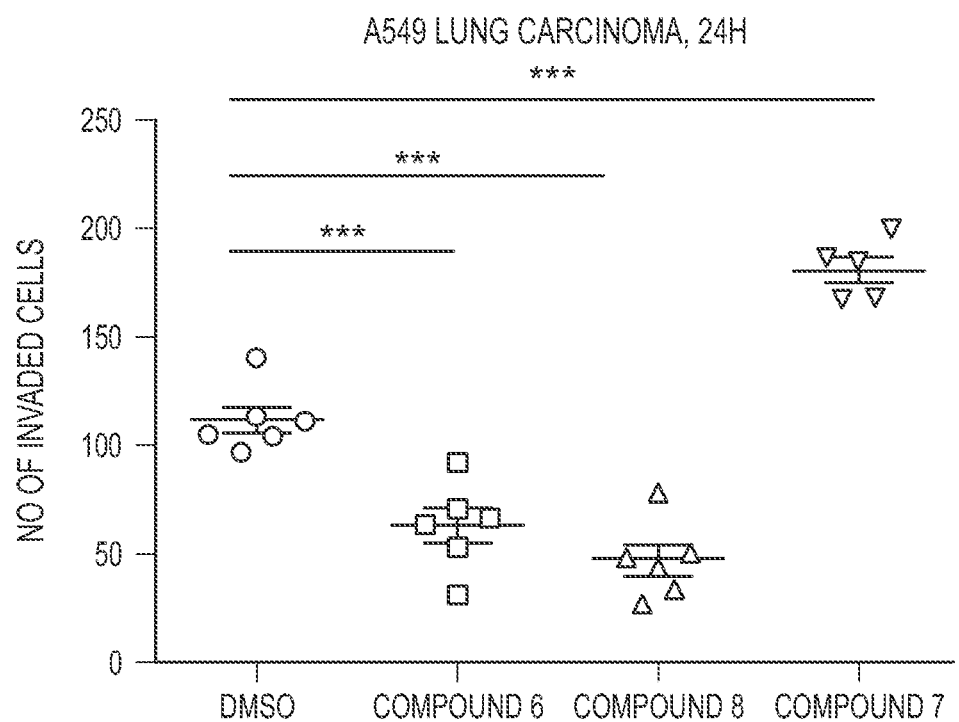
FIG. 4C is a graph showing quantitation of the number of invading A549 cells after treatment with 0.01-5 μM Compounds 6-8 for 72 hours (n=4, p<0.05).
Figure 4D:
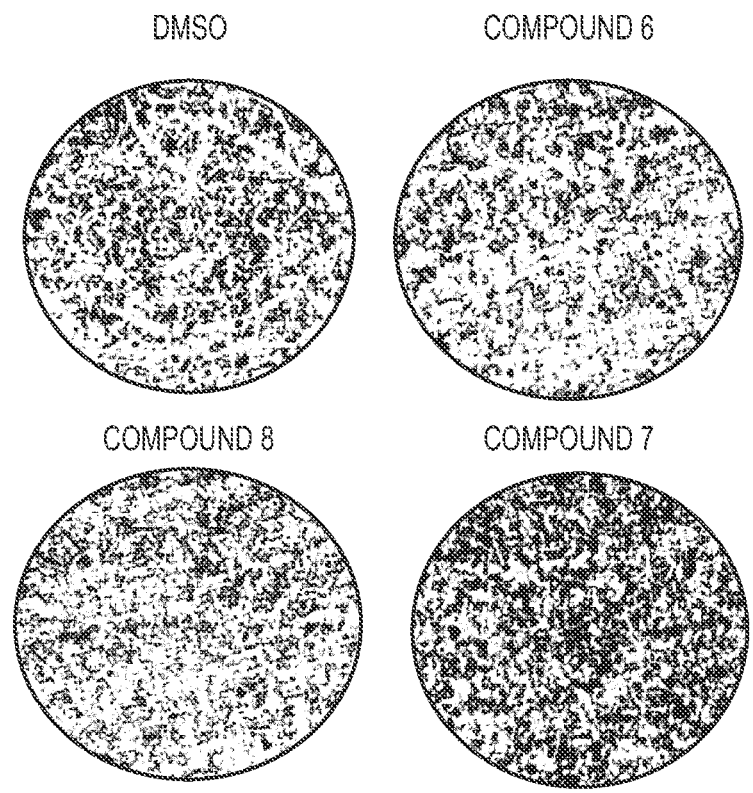
FIG. 4D are images of lower part of invasion chambers that were stained with crystal violet to show presence of invading A549 cells.

Other studies indicated high expression of STMN1 in cancer samples (see, e.g., Li et al., Pathology Oncology Research: 2015, 21(4):1013-20). As shown in FIGS. 4A and 4B, analysis of Geo profiles (as described in Chandran et al., *BMC cancer* 2007, 7:64) show high STMN1 and ASK1 mRNA levels in patient samples from advanced and metastatic prostate cancer. Because STMN1 is also strongly associated with microtubule stability and regulates invasion and migration of cancer cells (see, e.g., Williams et al., *Cancer Research* 2012, 72(20), 5407-17), experiments were conducted to investigate whether treatment with chalcone compounds affected cancer cell invasion. FIGS. 4C and 4D show that Compounds 6 and 8 strongly inhibited invasion of PC3 cells, while Compound 7 accelerated migration of PC3 cells through matrigel coated chambers to the serum chemoattractants as compared to untreated cells.

ASK1-Mediated Phosphorylation is Blocked by Chalcone Compounds

Figure 5A:
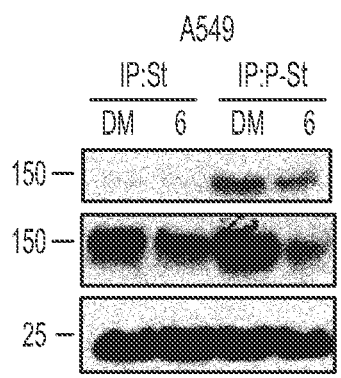
FIG. 5A is an image showing immunoprecipitation with antibody against STMN1 or P-STMN1 (Ser16) and immunoblotting with antibody against P-ASK1 (Ser83) in A549 cells treated with 1 μM Compound 6 or DMSO for 30 minutes.
Figure 5B:
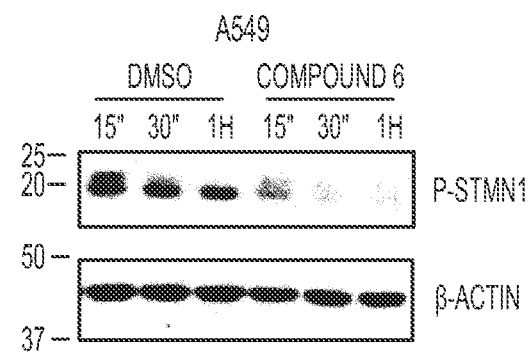
FIG. 5B is an image showing immunoblotting with antibody against P-STMN1 (Ser16) and STMN1 in A549 cells in the presence of DMSO or Compound 6 for 30 minutes.
Figure 5C:
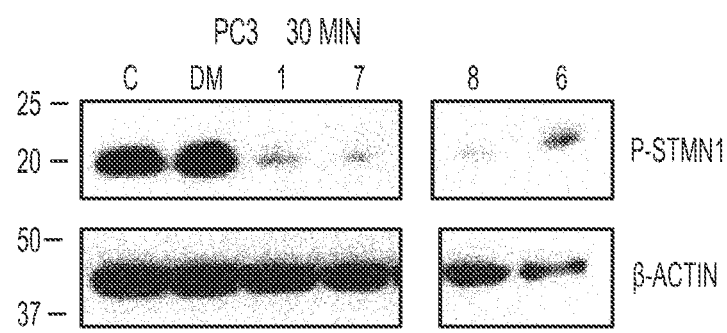
FIGS. 5C and 5D are images showing immunoblotting with antibody against P-STMN1 (Ser16) and STMN1 in PC3 cells untreated or in the presence of DMSO, Compound 6, Compound 7, or Compound 8 for 30 minutes.
Figure 5D:
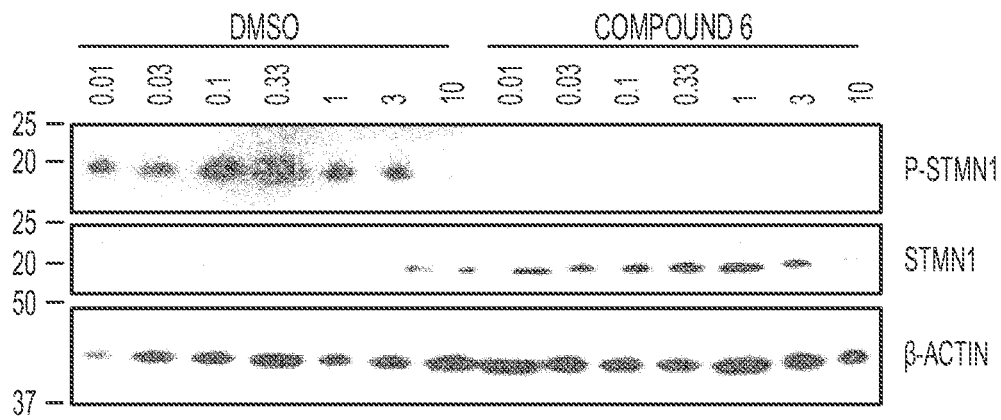
Figure 5E:
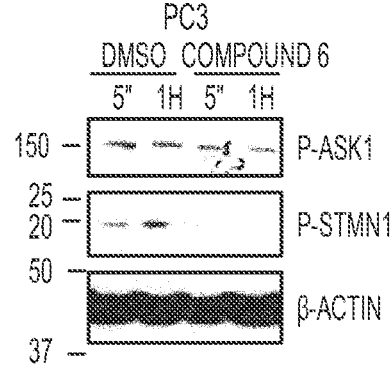
FIG. 5E is an image showing immunoblotting with antibodies against P-STMN1, P-JNK1, P-ASK1 in PC3 treated with DMSO and Compound 6 for 5 minutes or 1 hour.

Our above preliminary data suggest that the chalcone compounds described herein lead to stabilization of STMN1 and thus affect cancer cell viability. Further experiments were conducted to test whether the chalcone compounds influence stabilization of STMN1 by regulating its phosphorylation status. FIG. 5A shows that ASK1 kinase and STMN1 interaction is significantly blocked in response to short treatment with Compound 6. FIGS. 5B-5D show that the chalcone compounds diminished phosphorylation of STMN1 on Ser16, which is associated with higher expression and activity of STMN1 and its effects on microtubules stability. Without wishing to be bound by theory, it is believed that this phosphorylation is required for stability of STMN1. FIG. 5B shows that a modest regulation of P-ASK1 in response to treatment with chalceme compounds, suggesting that the compounds may either block activity of ASK1, its phosphorylation or its interaction with STMN1 thus leading to low phosphorylation of STMN1 and destabilization of microtubules and mitotic catastrophe (FIG. 5E).

Interaction of Chalcone Compounds with ASK1 Protein

Figure 6A:
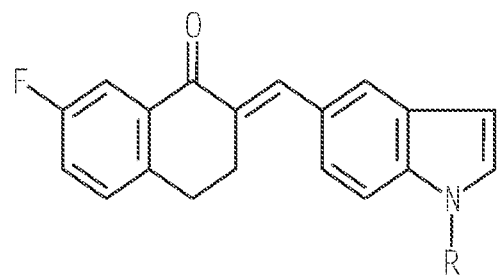
FIG. 6A shows a generic structure of certain exemplary chalcone compounds.
Figure 6B:
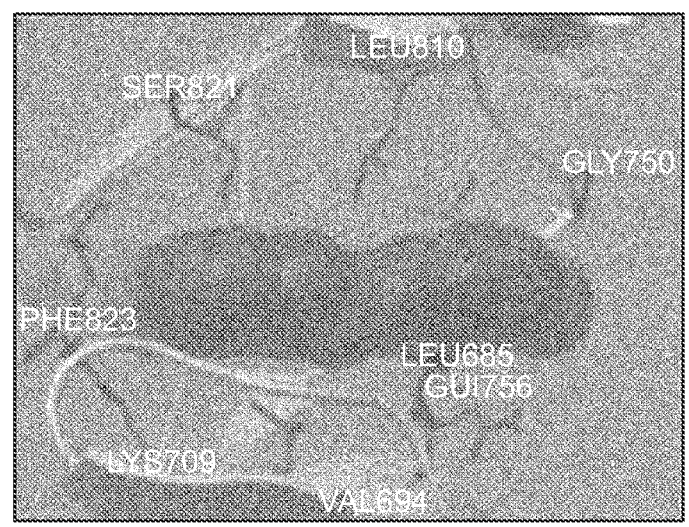
FIGS. 6B and 6C show key interactions between Compound 6 and ASK1 by using molecular dynamics simulation.
Figure 6C:
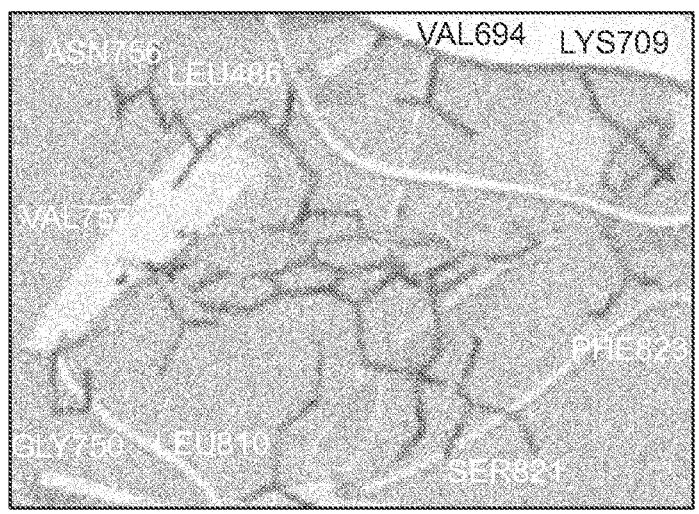
Figure 6D:
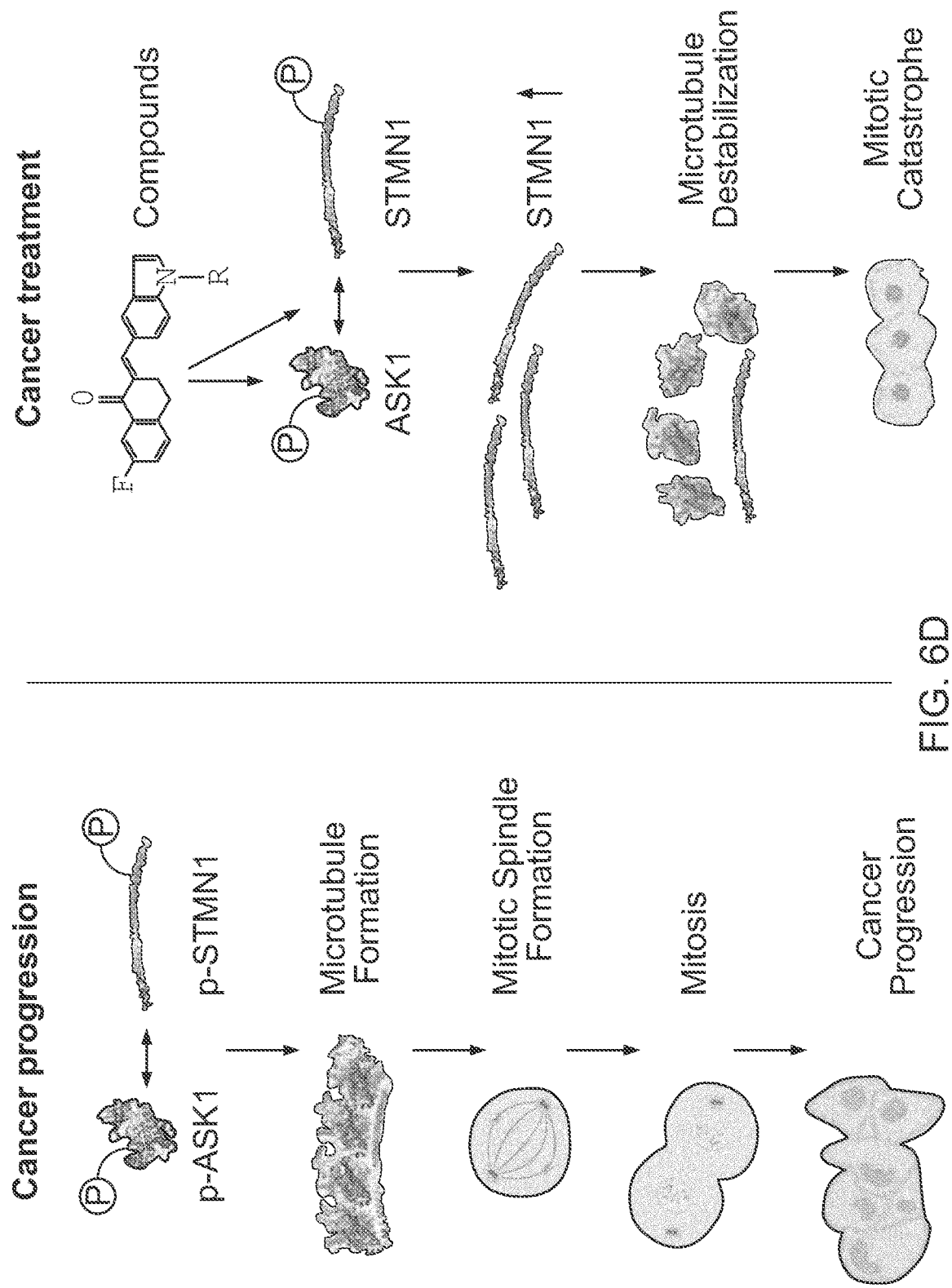
FIG. 6D illustrates involvement of ASK1 and STMN1 in cancer progression and proposed modulation of the ASK1/STMN1 pathway by the chalcone compounds described herein for cancer treatment.

The structure of chalcone compounds in our study are shown in FIG. 6A, where R is $CH_3$ in Compound 6; R is $C_2H_5$ in Compound 8; and R is H in Compound 7. Molecular dynamics (MD) simulation and computational modeling provided supportive evidence that chalcone compounds may target ASK1 directly to regulate its kinase activity and its downstream target, STMN1. The lowest energy binding pose of Compound 6 was found to occupy the ATP binding site in a similar position as staurosporine in the co-crystal structure as described in Bunkoczi et al., *Structure* 2007, 15(10), 1215-26. FIG. 6B shows that key interactions between Compound 6 and ASK1 include: (1) hydrogen bonding interactions between the indole moiety and the amino acid backbone of valine 757 and glycine 759 in addition to the side chain residue glutamine 756; (2) hydrophobic interactions between the surface of Compound 6 and valine 686, leucine 810, and valine 694; and (3) possible hydrogen bonding interactions between the fluorine (F) in Compound 6 with lysine 709 and phenylalanine 823. Similar binding interactions are observed in the staurosporine/ASK1 co-crystal structure. The lactam moiety of staurosporine is known to form two hydrogen bonds with methionine 754 and glutamine 756, which anchor the lactam moiety to the ASK1 amino acid backbone in a similar manner as the adenine base of ATP. FIG. 6C shows that, while the indole moiety of Compound 6 lies in a slightly different position, it is capable of acting as a hydrogen bond donor or acceptor to the same amino acid backbone. Additionally, similar hydrophobic interactions were found between staurosporine in the co-crystal structure and leucine 686, valine 694, and leucine 810. Compounds 7 and 8 both adopted similar binding poses as Compound 6 (data not shown). FIG. 6D illustrates involvement of ASK1 and STMN1 in cancer progression and proposed modulation of the ASK1/STMN1 pathway by the chalcone compounds described herein for cancer treatment.

Other embodiments are within the scope of the following claims.

What is claimed is:

1. A compound of formula (I) or a salt thereof:

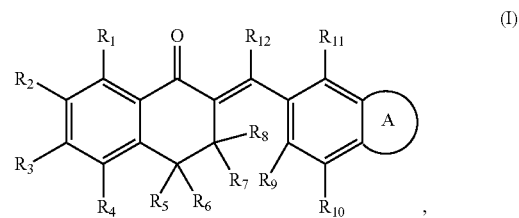

wherein

A is a five-membered ring, which optionally contains a heteroatom selected from the group consisting of N and S, and is optionally substituted with one or more substituents selected from the group consisting of halo, CN, OR, COOR, C(O)R, $C_1$-$C_{10}$ alkyl, $C_1$-$C_{10}$ arylalkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, and heteroaryl; and each of $R_1$, $R_2$, $R_3$, $R_4$, $R_5$, $R_6$, $R_7$, $R_8$, $R_9$, $R_{10}$, $R_{11}$, and $R_{12}$, independently, is H, halo, CN, OR', COOR', C(O)R', $C_1$-$C_{10}$ alkyl, $C_1$-$C_{10}$ arylalkyl, $C_2$-$C_{10}$ alkenyl, C$_2$-C$_{10}$ alkynyl, C$_3$-C$_{20}$ cycloalkyl, C$_3$-C$_{20}$ cycloalkenyl, C$_1$-C$_{20}$ heterocycloalkyl, C$_1$-C$_{20}$ heterocycloalkenyl, aryl, or heteroaryl;

in which each of R and R', independently, is H, C$_1$-C$_{10}$ alkyl, C$_3$-C$_{20}$ cycloalkyl, C$_3$-C$_{20}$ heterocycloalkyl, aryl, or heteroaryl.

2. The compound of claim 1, wherein A is a five-membered ring containing a heteroatom of N.

3. The compound of claim 1, wherein each of R$_5$, R$_6$, R$_7$, R$_8$, R$_9$, R$_{10}$, R$_{11}$, and R$_{12}$, is H.

4. The compound of claim 1, wherein the compound is a compound of formula (Ia):

(Ia)

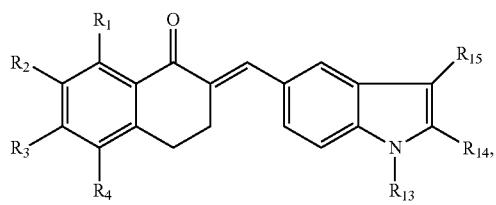

in which each of R$_1$, R$_2$, R$_3$, and R$_4$ is defined above; and each of R$_{13}$, R$_4$, and R$_{15}$, independently, is H, halo, CN, OR", COOR", C(O)R", C$_1$-C$_{10}$ alkyl, C$_1$-C$_{10}$ arylalkyl, C$_2$-C$_{10}$ alkenyl, C$_2$-C$_{10}$ alkynyl, C$_3$-C$_{20}$ cycloalkyl, C$_3$-C$_{20}$ cycloalkenyl, C$_1$-C$_{20}$ heterocycloalkyl, C$_1$-C$_{20}$ heterocycloalkenyl, aryl, or heteroaryl; R" being H, C$_1$-C$_{10}$ alkyl, C$_3$-C$_{20}$ cycloalkyl, C$_3$-C$_{20}$ heterocycloalkyl, aryl, or heteroaryl.

5. The compound of claim 4, wherein R$_2$ is H, F, Br, or CH$_3$O.

6. The compound of claim 4, wherein R$_3$ is H or CH$_3$O.

7. The compound of claim 4, wherein R$_{13}$ is H, CH$_3$, C$_2$H$_5$, CH$_2$Ph, CH$_3$O, C(O)CH$_3$, or COO(t-butyl).

8. The compound of claim 7, wherein the compound is

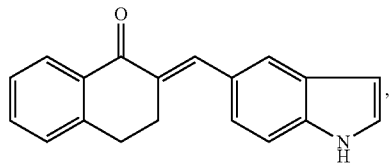

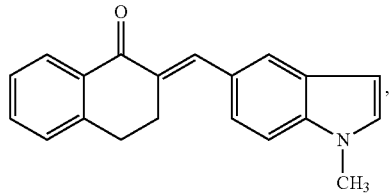

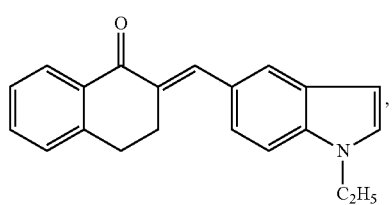

-continued

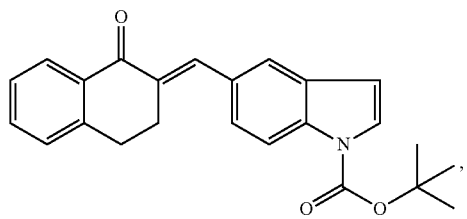

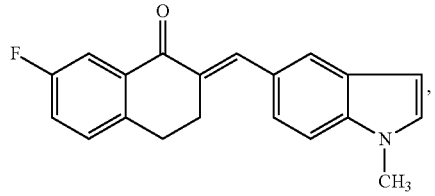

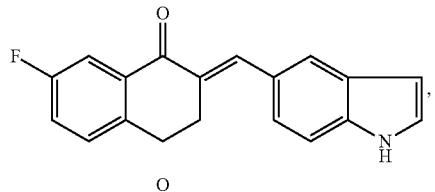

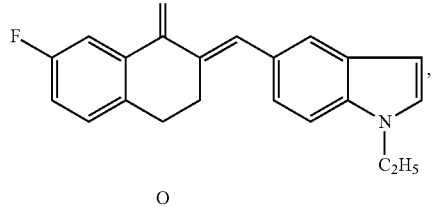

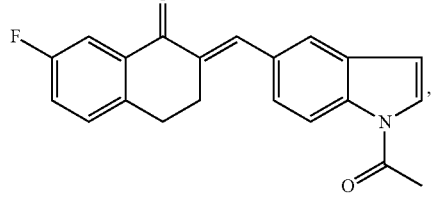

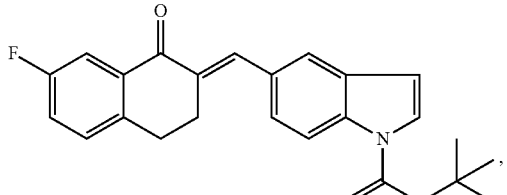

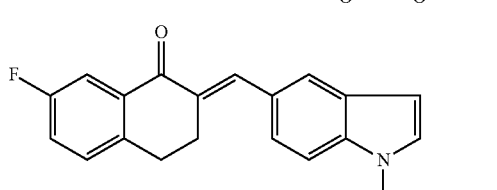

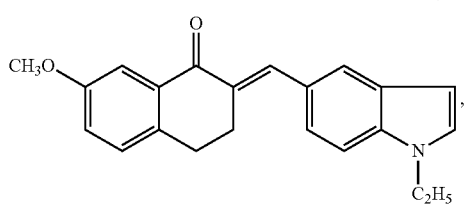

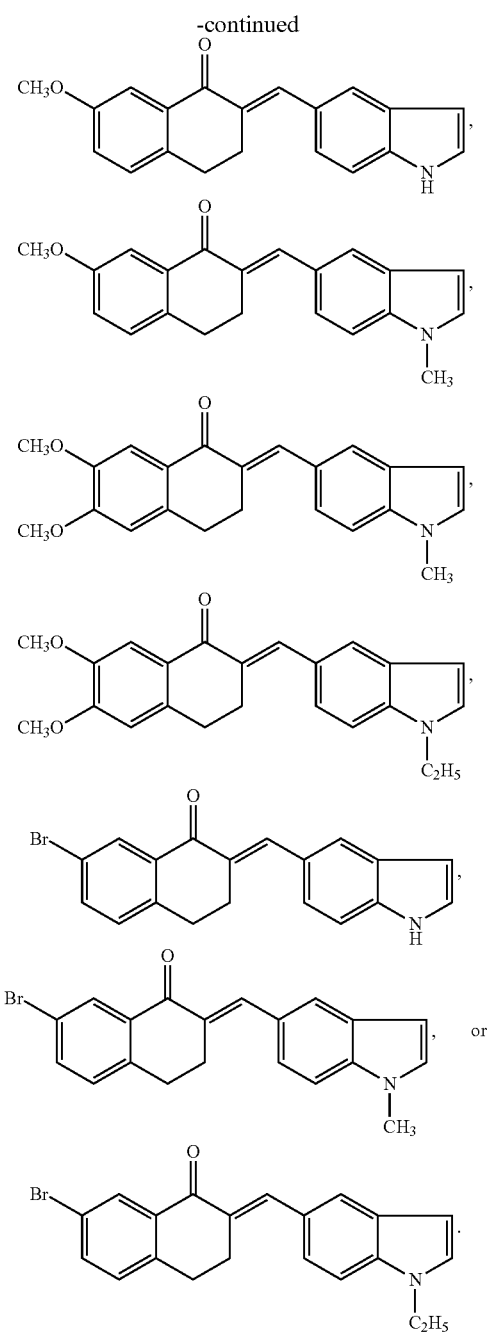

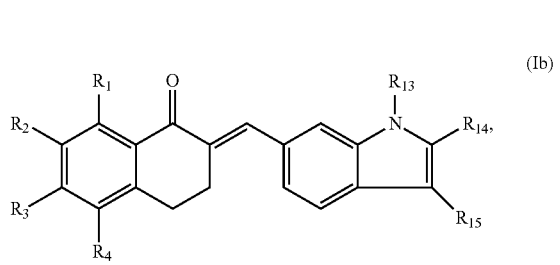

9. The compound of claim 1, wherein the compound is a compound of formula (Ib):

(Ib)

in which each of $R_1$, $R_2$, $R_3$, and $R_4$ is defined above; and each of $R_{13}$, $R_{14}$, and $R_{15}$, independently, is H, halo, CN, OR", COOR", C(O)R", $C_1$-$C_{10}$ alkyl, $C_1$-$C_{10}$ arylalkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl; R" being H, $C_1$-$C_{10}$ alkyl, $C_3$-$C_{20}$ cycloalkyl, $C_3$-$C_{20}$ heterocycloalkyl, aryl, or heteroaryl.

10. The compound of claim 9, wherein $R_2$ is H, Br, or $CH_3O$.

11. The compound of claim 9, wherein $R_3$ is H or $CH_3O$.

12. The compound of claim 9, wherein $R_{13}$ is $CH_3$.

13. The compound of claim 12, wherein the compound is

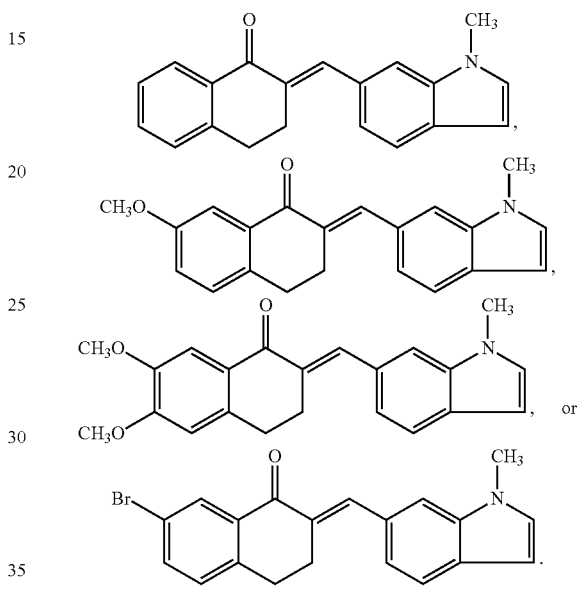

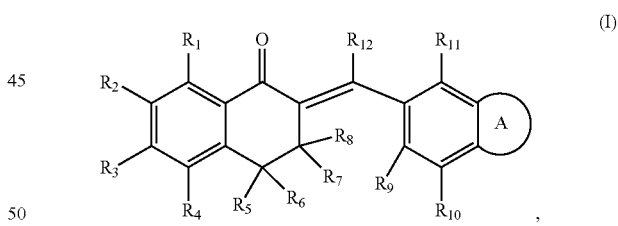

14. A pharmaceutical composition, a pharmaceutically acceptable carrier and a compound of formula (I) or a salt thereof:

(I)

wherein
A is a five-membered ring, which optionally contains a heteroatom, and is optionally substituted with one or more substituents selected from the group consisting of halo, CN, OR, COOR, C(O)R, $C_1$-$C_{10}$ alkyl, $C_1$-$C_{10}$ arylalkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, and heteroaryl; and
each of $R_1$, $R_2$, $R_3$, $R_4$, $R_5$, $R_6$, $R_7$, $R_8$, $R_9$, $R_{10}$, $R_{11}$, and $R_{12}$, independently, is H, halo, CN, OR', COOR', C(O)R', $C_1$-$C_{10}$ alkyl, $C_1$-$C_{10}$ arylalkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl;

in which each of R and R', independently, is H, $C_1$-$C_{10}$ alkyl, $C_3$-$C_{20}$ cycloalkyl, $C_3$-$C_{20}$ heterocycloalkyl, aryl, or heteroaryl.

15. A method for treating cancer in a subject in need thereof, comprising administering to the subject the pharmaceutical composition of claim 14 in an amount effective to treat the cancer;
  wherein the cancer is breast, stomach, lung, colorectal, prostate, liver, ovarian, uterine, pancreatic, rectum, mouth, esophagus, cervical, testicular, bladder, skin, bone, kidney, brain, head and neck, or throat cancer, leukemia, sarcoma, choriocarcinoma, or lymphoma.

16. The method of claim 15, wherein the cancer is prostate cancer or lung cancer.

17. A method of destabilizing microtubules in a cell, comprising contacting the cell with a compound of claim 1 in an amount sufficient to destabilize the microtubules in the cell.

18. A method of modulating stathmin activity in a cell, comprising contacting the cell with a compound of claim 1.

19. A method of modulating apoptosis signal-regulating kinase 1 (ASK1) activity in a cell, comprising contacting the cell with a compound of claim 1.

\* \* \* \* \*

UNITED STATES PATENT AND TRADEMARK OFFICE
CERTIFICATE OF CORRECTION

| | | |
|---|---|---|
| PATENT NO. | : 10,512,631 B2 | Page 1 of 1 |
| APPLICATION NO. | : 15/769301 | |
| DATED | : December 24, 2019 | |
| INVENTOR(S) | : Barbara Wegiel and Lijun Sun | |

It is certified that error appears in the above-identified patent and that said Letters Patent is hereby corrected as shown below:

On the Title Page

Column 2 (Abstract), Line 2, delete "[INSERT FORMULA]," and insert

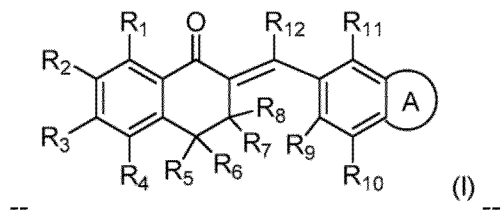

-- (I) --

In the Claims

In Column 17, Line 27, Claim 4, delete "$R_4$is" and insert -- $R_4$ is --

In Column 17, Line 28, Claim 4, delete "$R_4$," and insert -- $R_{14}$, --

In Column 19, Line 66, Claim 9, delete "$R_4$is" and insert -- $R_4$ is --

In Column 19, Line 67, Claim 9, delete "$R_4$" and insert -- $R_{14}$, --

Signed and Sealed this
Seventeenth Day of March, 2020

Andrei Iancu
*Director of the United States Patent and Trademark Office*